United States Patent [19]
Kawashima

[11] Patent Number: 5,817,019
[45] Date of Patent: Oct. 6, 1998

[54] DIAGNOSTIC ULTRASONIC IMAGING SYSTEM HAVING RUN EXTRACTING MEANS FOR EXTRACTING POINT CLOSEST TO START POINT OF SCANNING LINES

[75] Inventor: Tomonao Kawashima, Hachioji, Japan

[73] Assignee: Olympus Optical Co., Ltd., Tokyo, Japan

[21] Appl. No.: 840,229

[22] Filed: Apr. 11, 1997

[30] Foreign Application Priority Data

Apr. 15, 1996 [JP] Japan .................................. 8-092766
Jan. 14, 1997 [JP] Japan .................................. 9-004886

[51] Int. Cl.$^6$ ...................................................... A61B 8/00
[52] U.S. Cl. ........................................... 600/437; 128/916
[58] Field of Search ............................. 128/916; 600/437, 600/449

[56] References Cited

U.S. PATENT DOCUMENTS 5,413,106  5/1995  Fujita et al. .
5,454,371 10/1995  Fenster et al. .
5,497,776  3/1996  Yamazaki et al. .

FOREIGN PATENT DOCUMENTS 4-279156 10/1992 Japan .
6-30937   2/1994 Japan .

Primary Examiner—Marvin M. Lateef
Assistant Examiner—Maulin Patel
Attorney, Agent, or Firm—Armstrong, Westerman, Hattori, McLeland & Naughton

[57] ABSTRACT

Data provided by sound rays acquired by performing spiral scanning using ultrasonic waves is converted into image data through polar coordinate transformation. Data of slices is displayed and scanned along each scanning line from a start point of scanning lines to a far point. A point closest to the start point of scanning lines is extracted from each run of consecutive points at which luminance values exceed a threshold while a run of points having an unacceptable length is eliminated as a noise. Thus, the surface of an object is extracted.

21 Claims, 25 Drawing Sheets

Z AXIS OF LUMEN
(= AXIS OF INSERTED
ULTRASONIC PROBE)

FIG.23
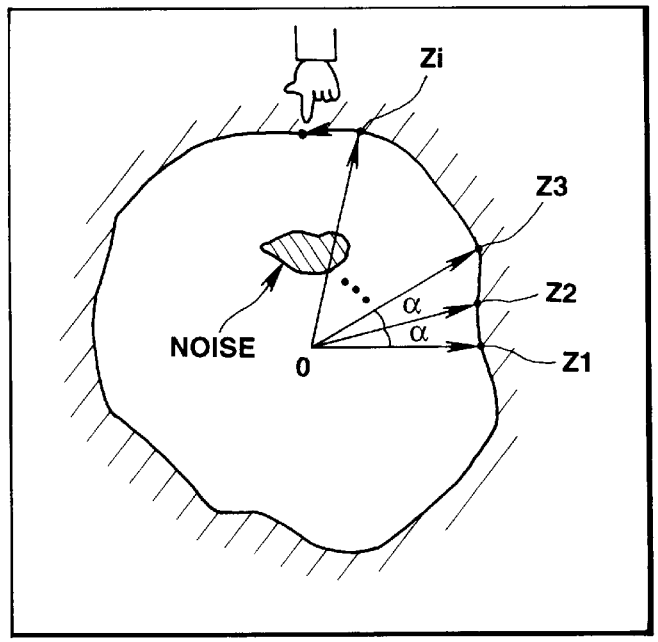
FIRST IMAGE
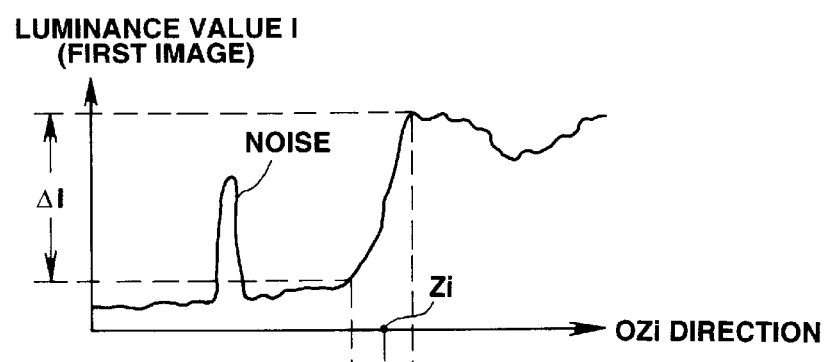
FIG.24A
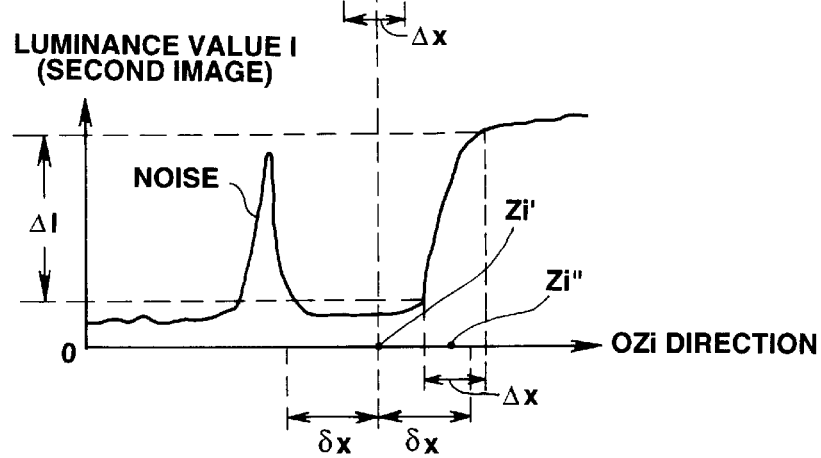
FIG.24B

DIAGNOSTIC ULTRASONIC IMAGING SYSTEM HAVING RUN EXTRACTING MEANS FOR EXTRACTING POINT CLOSEST TO START POINT OF SCANNING LINES

BACKGROUND OF THE INVENTION

1. Field of the Invention

The present invention relates to a diagnostic ultrasonic imaging system for constructing a three-dimensional image by transmitting and receiving ultrasonic waves to and from a living body, or more particularly, to a diagnostic ultrasonic imaging system having a run extracting means for extracting a point closest to a start point of scanning lines from each run of consecutive points at which data values are larger than a threshold.

2. Description of the Related Art

In recent years, diagnostic ultrasound systems including the one disclosed in Japanese Unexamined Patent Publication No. 6-30937, which carry out three-dimensional scanning such as spiral scanning so as to transmit ultrasonic waves to a living body and receive echoes from the living body, acquire data provided by the echoes emanating from a region to be examined, and thus visualize the region to be examined in the living body three-dimensionally, have been proposed.

U.S. Pat. No. 5,497,776 and Japanese Unexamined Patent Publication No. 4-279156 have disclosed systems in which data provided by echoes emanating from a living body is displayed three-dimensionally and synthesized with image data of the surface of a body cavity, which is processed for perspective representation or shaded by glow shading, in order to express the contour of the living body stereoscopically while holding the gray-scale levels represented by the echo data and needed for medical diagnosis.

In the system disclosed in the U.S. Pat. No. 5,497,776, a display screen on a monitor is quartered, and a desired slice can be set interactively by setting the position of the slice using a trackball or the like.

In the system disclosed in the Japanese Unexamined Patent Publication No. 4-279156, the surface of an organ is automatically extracted by processing data coincident with a line of sight relative to a threshold. Moreover, the surface is colored in order to provide changes in hue for depth perception and to thus express the surface stereoscopically.

Furthermore, in the systems disclosed in the U.S. Pat. No. 5,497,776 and Japanese Unexamined Patent Publication No. 4-279156, the display color of the surface of an organ in a three-dimensional image is determined in terms of the distance of the surface or the stereoscopic representation of the contour of the organ, and often has no relation to the original color of the organ recognized in an optical image.

However, in the system disclosed in the Japanese Unexamined Patent Publication No. 4-279156, data is processed relative to a threshold, and the surface of an organ is extracted by judging whether or not a luminance value is larger than a certain value. This poses a problem that a noise existent outside the organ may be taken for part of the surface of the organ, and then extracted.

The system disclosed in the Japanese Unexamined Patent Publication No. 4-279156 has a drawback that it cannot be checked if surface extraction has been carried out properly.

The system disclosed in the Japanese Unexamined Patent Publication No. 4-279156 has a drawback that part of a surface improperly extracted cannot be corrected.

The system disclosed in the U.S. Pat. No. 5,497,776 is configured so that the position of a slice is set merely by setting the position of an intersection between slicing lines. The slice cannot therefore be defined on a plane other than a plane parallel to the slicing lines. This poses a problem that a slice containing a lesion whose position coincides with a position in an oblique area such as a right-hand lower area in a tomographic image produced perpendicularly to the axis of a lumen cannot be observed, and therefore the depth of the lesion cannot be assessed.

The system disclosed in the U.S. Pat. No. 5,497,776 has a drawback that since slices are indicated merely by setting the slicing lines in a quartered display screen on a monitor, it is hard to distinguish part of the display screen used to display a three-dimensional image and the other part thereof unused to display the three-dimensional image, and it is hard to recognize the relationship of correspondence between these parts.

The system disclosed in the U.S. Pat. No. 5,497,776 has a drawback that an angle of light used for shading cannot be modified, and some shapes cannot be expressed stereoscopically.

The system disclosed in the U.S. Pat. No. 5,497,776 does not include a means for use in designating the direction of a line of sight. Therefore, even after the direction of a line of sight in which a three-dimensional image is oriented is changed in an effort to make a region of interest such as a lesion more clearly visible, and then two-dimensional projection is performed again, the region of interest may not be able to be clearly visualized. This poses a problem that projection must be carried out a plurality of times until a desired three-dimensional image is constructed.

Moreover, assuming that a physician judges the progress of a lesion including the depth thereof from data provided by echoes, and compares the image of a surface with an optical image such as an endoscopic image in terms of the contour of the lesion and the like, since the system disclosed in the U.S. Pat. No. 5,497,776 displays both a three-dimensionally displayed image and the image of a surface in gray scale, it is difficult for the operator to determine whether areas in the three-dimensional image are representations of image data holding the gray-scale levels indicated by echoes emanating from a living body or representations of the image data of the surface which is shaded or to which stereoscopic information such as a contour is appended.

Furthermore, the systems disclosed in the U.S. Pat. No. 5,497,776 and Japanese Unexamined Patent Publication No. 4-279156 have a drawback that since the display color of the image of the surface of an organ in a three-dimensional image is determined in terms only of the distance to the surface or the stereoscopic representation of the contour of the surface, and has no relation to the real color of the organ discernible in an optical image, a person other than an operator have difficulty in recognizing a region in a body cavity visualized in the three-dimensional image.

OBJECTS AND SUMMARY OF THE INVENTION

The first object of the present invention is to provide a diagnostic ultrasonic imaging system capable of expressing the surface of a desired object accurately without being interfered by a noise or the like.

The second object of the present invention is to provide a diagnostic ultrasonic imaging system making it possible to check if extracting the surface of an object is carried out properly.

The third object of the present invention is to provide a diagnostic ultrasonic imaging system capable of correcting improperly-extracted part of the surface of an object.

The fourth object of the present invention is to provide a diagnostic ultrasonic imaging system making it possible to properly set a slice using a tomographic image irrespective of the position of a lesion, and assess the depth of the lesion.

The fifth object of the present invention is to provide a diagnostic ultrasonic imaging system making it possible to set slices so that part of tomographic images used to construct a three-dimensional image can be distinguished from the other part thereof unused to construct the three-dimensional image, and the relationship of correspondence between the parts can be grasped readily.

The sixth object of the present invention is to provide a diagnostic ultrasonic imaging system capable of expressing the surface of a desired object stereoscopically and making it possible to set an angle of light for an intuitively and anatomically better understanding.

The seventh object of the present invention is to provide a diagnostic ultrasonic imaging system making it possible to set the angle of a line of sight more easily so that a region of interest such as a lesion can be discerned more clearly.

The eighth object of the present invention is to provide a diagnostic ultrasonic imaging system making it possible to distinguish data provided by echoes from image data of a surface.

The ninth object of the present invention is to provide a diagnostic ultrasonic imaging system capable of associating the display color of the image of the surface of an organ with the real color of the organ discernible from an optical image, and making it possible to view a more realistic three-dimensional image.

For accomplishing the first object, a diagnostic ultrasonic imaging system has the components described in (1) below.

(1) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a surface point extracting means for extracting points defining the surface of a desired object from the three-dimensional data stored in the three-dimensional echo data memory means;

a shading means for shading data of a surface defined with the points extracted by the surface point extracting means;

a synthesizing means for synthesizing data of the slices whose positions are set by the slice position setting means and data of the surface shaded by the shading means so as to construct a three-dimensional image; and a display means for displaying the three-dimensional image constructed by the synthesizing means.

The diagnostic ultrasonic imaging system is characterized in that the surface point extracting means includes a run extracting means for scanning the three-dimensional echo data along each scanning line from a start point of scanning lines to a far point, and extracting a point closest to the start point of scanning lines from each run of consecutive points, at which luminance values exceed a certain threshold, having a length larger than a set length.

According to the above configuration, the slice position setting means sets the positions of desired slices using the three-dimensional echo data stored in the three-dimensional echo data memory means.

The run extracting means in the surface point extracting means scans the three-dimensional echo data along each scanning line from the start point of scanning lines to a far point, extracts a point closest to the start point of scanning lines from each run of consecutive points, at which luminance values exceed a certain threshold, having a length larger than a set length. Thus, points defining the surface of a desired object are extracted from the three-dimensional echo data stored in the three-dimensional echo data memory means.

The shading means shades data of a surface defined with the points extracted by the surface point extracting means.

The synthesizing means synthesizes data of the slices and data of the surface so as to construct a three-dimensional image. The display means displays the three-dimensional image.

For accomplishing the second object, a diagnostic ultrasonic imaging system has the components listed below in (2).

(2) An ultrasonic probe for transmitting ultrasonic waves to a living body, receiving echoes from the living body, and producing a plurality of consecutive ultrasonic tomographic images depicting a three-dimensional area;

a three-dimensional echo data memory means for storing data that is provided by the echoes emanating from the three-dimensional area and represents the plurality of consecutive ultrasonic tomographic images produced by the ultrasonic probe;

a slice position setting means for setting the positions of desired slices using the three-dimensional echo data stored in the three-dimensional echo data memory means;

a surface point extracting means for extracting points defining the surface of a desired object from the three-dimensional echo data stored in the three-dimensional echo data memory means;

a shading means for shading data of a surface defined with the points extracted by the surface point extracting means;

a synthesizing means for synthesizing data of the slices whose positions are specified by the slice position setting means and data of the surface shaded by the shading means so as to construct a three-dimensional image; and a display means for displaying the three-dimensional image constructed by the synthesizing means.

The diagnostic ultrasonic imaging system is characterized in that the surface point extracting means includes a boundary superposing means for superposing the extracted points defining the surface of an object as a boundary on all of the plurality of consecutive ultrasonic tomographic images or on a specified ultrasonic tomographic images.

According to the foregoing configuration, the slice position setting means sets the positions of desired slices using the three-dimensional echo data stored in the three-dimensional echo data memory means.

The boundary superposing means in the surface point extracting means superposes the extracted points defining the surface of an object as a boundary on all of the plurality of consecutive ultrasonic tomographic images or on a specified ultrasonic tomographic image. While a user is checking a point to be extracted, the point defining the surface of a desired object is extracted from the three-dimensional echo data stored in the three-dimensional echo data memory means.

The shading means shades data of a surface defined with the points extracted by the surface point extracting means.

The synthesizing means synthesizes data of the slices and data of the surface so as to construct a three-dimensional image. The display means displays the three-dimensional image.

For accomplishing the third object, a diagnostic ultrasonic imaging system has the components listed below in (3).

(3) The same components as those of the diagnostic ultrasonic imaging system listed in (2), whereas the surface point extracting means includes a boundary correcting means for correcting a boundary superposed by the boundary superposing means, and thus corrects positions defining the surface of an object to be extracted according to the boundary corrected by the boundary correcting means.

According to the above configuration, the slice position setting means sets the positions of desired slices using the three-dimensional echo data stored in the three-dimensional echo data memory means.

The boundary correcting means in the surface point extracting means corrects a boundary superposed by the boundary superposing means. The surface point extracting means then corrects points defining the surface of an object to be extracted according to the boundary corrected by the boundary correcting means. Thus, points defining the surface of a desired object can be extracted properly from the three-dimensional data stored in the three-dimensional data memory means.

The shading means shades data of a surface defined with the points extracted by the surface point extracting means.

The synthesizing means synthesizes data of the slices and data of the surface so as to construct a three-dimensional image. The display means displays the three-dimensional image.

For accomplishing the fourth object, a diagnostic ultrasonic imaging system has the components listed below in (4).

(4) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a synthesizing means for constructing a three-dimensional image using data of the slices whose positions are set by the slice position setting means; and a display means for displaying the three-dimensional image constructed by the synthesizing means.

The diagnostic ultrasonic imaging system is characterized in that:

the slice position setting means includes: a tomographic image constructing means for constructing a plurality of tomographic images depicting differently-oriented slices using image data of the three-dimensional echo data;

a slicing line moving means for moving slicing lines indicating the positions of slices in the plurality of tomographic images constructed by the tomographic image constructing means; and a tomographic image turning means for turning a specified tomographic image among the plurality of tomographic images constructed by the tomographic image constructing means.

Among the plurality of tomographic images constructed by the tomographic image constructing means, tomographic images other than the specified tomographic image are modified responsively to the turn of the specified tomographic image made by the tomographic image turning means.

According to the foregoing configuration, the tomographic image constructing means in the slice position setting means constructs a plurality of tomographic images depicting differently-oriented slices using image data of the three-dimensional echo data, the slicing line moving means moves slicing lines indicating the positions of slices in the plurality of tomographic images constructed by the tomographic image constructing means, and the tomographic image turning means turns a specified tomographic image among the plurality of tomographic images constructed by the tomographic image constructing means. Among the plurality of tomographic images constructed by the tomographic image constructing means, tomographic images other than the specified tomographic image are modified responsively to the turn of the specified tomographic image made by the tomographic image turning means. Thus, the positions of desired slices are set using the three-dimensional echo data stored in the three-dimensional echo data memory means.

The synthesizing means constructs a three-dimensional image using data of the slices whose positions are set by the slice position setting means. The display means displays the three-dimensional image.

For accomplishing the fifth object, a diagnostic ultrasonic imaging system has the components listed below in (5).

(5) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a synthesizing means for constructing a three-dimensional image using data of the slices whose positions are set by the slice position specifying means; and a display means for displaying the three-dimensional image constructed by the synthesizing means.

The diagnostic ultrasonic imaging system is characterized in that the slice position setting means includes:

a tomographic image constructing means for constructing a plurality of tomographic images depicting differently-oriented slices using image data of the three-dimensional data; and a slicing line moving means for moving slicing lines indicating the positions of slices in a plurality of tomographic images constructed by the tomographic image constructing means.

The tomographic image constructing means includes a masking means for displaying data used by the synthesizing means for constructing a three-dimensional image, and the other data in different forms.

According to the foregoing configuration, the tomographic image constructing means in the slice point setting means constructs a plurality of tomographic images depicting differently-oriented slices using image data of the three-dimensional echo data, the slicing line moving means moves slicing lines indicating the positions of slices in the plurality of tomographic images constructed by the tomographic image constructing means, and the masking means displays data used by the synthesizing means for constructing the three-dimensional image and the other data in different forms. Thus, the positions of desired slices can be set using the three-dimensional echo data stored in the three-dimensional echo data memory means.

The synthesizing means uses data of the slices whose positions are set by the slice position setting means to construct a three-dimensional image.

The display means displays the three-dimensional image.

For accomplishing the sixth object, a diagnostic ultrasonic imaging system has the components listed below in (6).

(6) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a surface point extracting means for extracting points defining the surface of a desired object from the three-dimensional echo data stored in the three-dimensional echo data memory means;

a shading means for shading data of a surface defined with the points extracted by the surface point extracting means;

a synthesizing means for synthesizing data of the slices whose positions are set by the slice position setting means and data of the surface shaded by the shading means so as to construct a three-dimensional image; and a display means for displaying the three-dimensional image constructed by the synthesizing means.

The diagnostic ultrasonic imaging system is characterized in that the shading means includes a light angle setting means for setting angles defining light used for shading as angles in a coordinate system having the axis of a lumen in a living body or the axis of an inserted ultrasonic probe as one of its coordinate axes, and that the display means displays the angles defining light in the coordinate system having the axis of a lumen in a living body or the axis of an inserted ultrasonic probe as one of its coordinate axes.

According to the foregoing configuration, the slice position setting means sets the positions of desired slices using the three-dimensional echo data stored in the three-dimensional echo data memory means.

The surface point extracting means extracts points defining the surface of a desired object from the three-dimensional echo data stored in the three-dimensional echo data memory means.

The light angle setting means in the shading means sets angles defining light used for shading as angles in a coordinate system having the axis of a lumen in a living body or the axis of an inserted ultrasonic probe as one of its coordinate axes. The display means displays a three-dimensional image, and displays the angles defining light in the coordinate system having the axis of a lumen in a living body or the axis of an inserted ultrasonic probe as one of its of coordinate axes. Data of a surface defined with the points extracted by the surface point extracting means is thus shaded.

The synthesizing means synthesizes data of the slices and data of the surface so as to construct a three-dimensional image. The display means displays the three-dimensional image.

For accomplishing the seventh object, a diagnostic ultrasonic imaging system has the components listed in (7) below.

(7) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a surface point extracting means for extracting points defining the surface of a desired object from the three-dimensional echo data stored in the three-dimensional echo data memory means;

a shading means for shading data of a surface defined with the points extracted by the surface point extracting means;

a synthesizing means for synthesizing data of the slices whose positions are set by the slice position setting means and data of the surface shaded by the shading means so as to construct a three-dimensional image; and a display means for displaying the three-dimensional image constructed by the synthesizing means.

The diagnostic ultrasonic imaging system further comprises a coordinate transforming means for transforming coordinates of data of the slices whose positions are set by the slice position setting means and of data of the surface defined with the points extracted by the surface point extracting means, and is characterized in that:

the coordinate transforming means includes a line-of-sight angle setting means for setting angles defining a line of sight or the direction of a line of sight, in which the three-dimensional image is displayed, as angles in a coordinate system having the axis of a lumen in a living body or the axis of an inserted ultrasonic probe as one of its coordinate axes; and the display means displays the angles defining a line of sight in the coordinate system having the axis of a lumen in a living body or the axis of an inserted ultrasonic probe as one of its coordinate axes.

According to the foregoing configuration, the slice position setting means sets the positions of desired slices using the three-dimensional echo data stored in the three-dimensional echo data memory means.

The surface point extracting means extracts points defining the surface of a desired object from the three-dimensional echo data stored in the three-dimensional echo data memory means.

The shading means shades data of a surface defined with the points extracted by the surface point extracting means.

The line-of-sight angle setting means in the coordinate transforming means sets angles defining a line of sight or the direction of a line of sight, in which a three-dimensional image is displayed, as angles in a coordinate system having the axis of a lumen in a living body or the axis of an inserted ultrasonic probe as one of its coordinate axes. The display means displays the angles defining a line of sight in the coordinate system having the axis of a lumen in a living body or the axis of an inserted ultrasonic probe one of its coordinate axes. Thus, the coordinates indicated with the data of a plane whose position is specified by the slice position specifying means and the coordinates indicated with the data of a surface identified by the surface identifying means are transformed.

The synthesizing means synthesizes data of the slices and data of the surface so as to construct a three-dimensional image. The display means displays the three-dimensional image.

For accomplishing the eighth object, a diagnostic ultrasonic imaging system has the components listed in (8) below.

(8) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a surface point extracting means for extracting points defining the surface of a desired object from the three-dimensional echo data stored in the three-dimensional echo data memory means;

a shading means for shading data of a surface defined with the points extracted by the surface point extracting means;

a synthesizing means for synthesizing data of the slices whose positions are set by the slice position setting means and data of the surface shaded by the shading means so as to construct a three-dimensional image; and a display means for displaying the three-dimensional image constructed by the synthesizing means.

The diagnostic ultrasonic imaging system is characterized in that:

the synthesizing means includes a slice-surface boundary superposing means for superposing a boundary line between data of the slices and data of the surface as a slice-surface boundary line on the three-dimensional image; and the display means displays the three-dimensional image on which the slice-surface boundary line is superposed by the slice-surface boundary superposing means.

According to the foregoing configuration, the slice position setting means sets the positions of desired slices using the three-dimensional echo data stored in the three-dimensional echo data memory means.

The surface point extracting means extracts points defining the surface of a desired object from the three-dimensional echo data stored in the three-dimensional echo data memory means.

The shading means shades data of a surface defined with the points extracted by the surface point extracting means.

The synthesizing means synthesizes data of the slices and data of the surface so as to construct a three-dimensional image. The slice-surface boundary superposing means superposes a boundary line between data of the slices and data of the surface as a slice-surface boundary line on the three-dimensional image.

The display means displays the three-dimensional image on which the slice-surface boundary line is superposed by the slice-surface boundary superposing means.

For accomplishing the ninth object, a diagnostic ultrasonic system has the components listed in (9) below.

(9) A three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in the three-dimensional echo data memory means;

a surface point extracting means for extracting points defining the surface of a desired object from the three-dimensional echo data stored in the three-dimensional echo data memory means;

a shading means for shading data of a surface defined with the points extracted by the surface point extracting means;

a synthesizing means for synthesizing data of the slices whose positions are set by the slice position setting means and data of the surface shaded by the shading means so as to construct a three-dimensional image; and a display means for displaying the three-dimensional image constructed by the synthesizing means.

The diagnostic ultrasonic imaging system is characterized in that the shading means shades data of a surface using the color of the surface of an organ as a display color.

According to the foregoing configuration, the slice position setting means sets the positions of desired slices using the three-dimensional echo data stored in the three-dimensional echo data memory means.

The surface point extracting means extracts points defining the surface of a desired object from the three-dimensional echo data stored in the three-dimensional echo data memory means.

The shading means shades data of a surface defined with the points extracted by the surface point extracting means using the color of the surface of an organ as a display color.

The synthesizing means synthesizes data of the slices and data of the surface so as to construct a three-dimensional image.

The display means displays the three-dimensional image.

BRIEF DESCRIPTION OF THE DRAWINGS

FIG. 1 is a block diagram showing the configuration of a diagnostic ultrasonic imaging system of the first embodiment;

FIG. 2 is a flowchart describing the contents of image processing performed by a CPU and image processor;

FIG. 3 is a flowchart describing the contents of setting of the positions of slices in FIG. 2;

FIG. 4 is a diagram showing an exemplary example of four ultrasonic images depicting slicing planes;

FIG. 5 is a diagram showing a simple three-dimensional image produced without surface point extraction;

FIG. 6 is a diagram showing the same ultrasonic images as those shown in FIG. 4 with parts of the images unused to construct the image shown in FIG. 5;

FIG. 7 shows sub screens used to set the direction of a line of sight;

FIG. 8 is an explanatory diagram spatially showing angles shown in FIG. 7;

FIG. 9 is a flowchart describing the contents of the processing of extracting points defining a surface described in FIG. 2;

FIG. 10 is an explanatory diagram showing scanning started at a scanning start point for extracting points defining a surface;

FIG. 11 is a flowchart describing the processing of shading;

FIG. 12 is an explanatory diagram of the processing of shading;

FIG. 13 shows sub screens for setting in which the set value of the direction of light is displayed;

FIG. 14 is an explanatory diagram spatially showing the angles shown in FIG. 13;

FIG. 15 is a diagram showing four images with parts of the images unused to display a three-dimensional image hatched;

FIG. 16 is a diagram showing a three-dimensional image constructed finally;

FIG. 23 is an explanatory diagram showing a scene of manually tracing points defining a boundary using the first image;

FIGS. 24A and 24B are explanatory diagrams concerning calculation of the first gradients at points traced using the first image and the second gradients at corresponding points traced using the second image;

DESCRIPTION OF THE PREFERRED EMBODIMENTS

Figure 1:
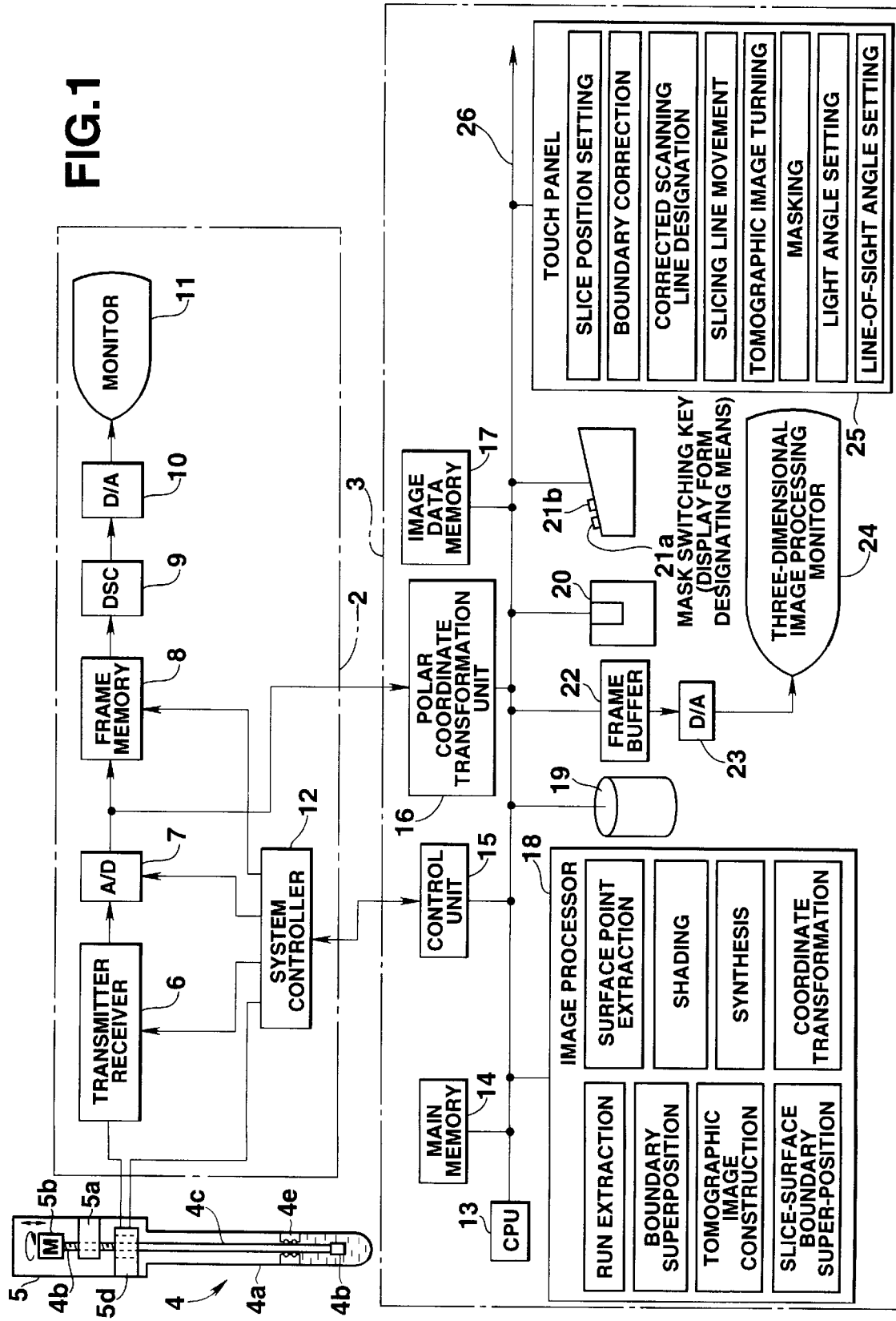
FIGS. 1 to 16 relate to the first embodiment of the present invention.

Referring to the drawings, embodiments of the present invention will be described below.

As shown in FIG. 1, a diagnostic ultrasonic imaging system 1 of the first embodiment comprises an ultrasonic viewer 2 for transmitting ultrasonic waves, receiving echoes, and displaying images provided by the echoes in real time, and an image processing unit 3 for processing images for three-dimensional image display on the basis of data provided by the echoes received by the ultrasonic viewer 2. The diagnostic ultrasonic imaging system 1 further comprises an ultrasonic probe 4 in which an ultrasonic transducer 4b for transmitting ultrasonic waves and receiving echoes are incorporated, and which includes an insertional part 4a to be inserted into a body cavity and has a means for enabling spiral scanning by the ultrasonic transducer 4b. A driver 5 for driving the ultrasonic probe 4 is connected to the ultrasonic viewer 2.

The ultrasonic viewer 2 comprises a transmitter receiver 6 for transmitting ultrasonic waves or receiving echoes via the driver 5, an A/D converter 7 for converting echoes received by the transmitter receiver 6 into digital data, a frame memory 8 for storing data converted by the A/D converter 7, a digital scan converter 9 (DSC) for converting data stored in the frame memory 8 into image data conformable to a given television system, a monitor 11 for inputting an output image signal of the D/A converter 10 and displaying an image in real time, and a system controller 12 for controlling the driver 5, transmitter receiver 6, A/D converter 7, and frame memory 8.

The image processing unit 3 comprises a CPU 13 responsible for control of image processing and the like, a main memory 14 for storing data resulting from various kinds of image processing, a control unit 15 for transmitting or receiving instructions to or from the system controller 12, a polar coordinate transformation unit 16 for transforming data of consecutive sound rays provided by the ultrasonic viewer 2 into a plurality of consecutive two-dimensional images, an image data memory 17 for storing image data provided by the polar coordinate transformation unit 16, an image processor 18 for carrying out various kinds of image processing; such as, surface point extraction, shading, synthesis, coordinate transformation, run extraction, boundary superposition, tomographic image construction, and slice-surface boundary superposition at a high speed, a first external storage device 19 for storing information including programs and backup data, such as, a hard disk, a second external storage device 20 for backing up the contents of the first external storage device 19, such as, a magneto-optical disk, an operation terminal 21 such as a keyboard, a frame buffer 22 for temporarily storing data having undergone image processing, a D/A converter 23 for converting an output image signal of the frame buffer 22 into an analog signal, a three-dimensional image processing monitor 24 for inputting an output image signal of the D/A converter 23 and displaying a three-dimensional image resulting from image processing, and a cover-like touch panel 25 placed on the display surface of the three-dimensional image processing monitor 24 and used to set an image display area or entering any other information.

Formed on the operation surface of the operation terminal 21 are a mask switching key 21a and a simple three-dimensional image construction key 21b. Since the touch panel 25 is adopted, the CPU 13 is designed to identify a point on the three-dimensional image processing monitor 24 touched with a user's finger. The components of the image processing unit 3 are interconnected over a data transfer bus 26, whereby image data and the like can be transferred.

A shaft 4c runs through the insertional part 4a of the ultrasonic probe 4. The ultrasonic transducer 4b is attached to the tip of the shaft 4c. A male thread 4d is formed as the rear part of the shaft 4c. The male thread 4d is passed through a screw hole of a support member 5a in the driver 5. A motor 5b is attached to the back end of the male thread 4d.

By rotating the motor 5b, the ultrasonic transducer 4b located at the tip of the shaft 4c transmits ultrasonic waves radially. The ultrasonic transducer 4b and motor 5b to be rotated transmit signals including a driving signal via a slip ring 5d. The shaft 4c is supported by a watertight bearing 4e.

In this embodiment, as described later, a surface point extracting means is included. The surface point extracting means scans the three-dimensional data output from the ultrasonic viewer 2 along each scanning line from the start point of scanning lines to a far point, and extracts a point closest to the start point of scanning lines from a run of points, at which luminance values exceed a certain threshold set for surface extraction, having a length larger than a given length or a threshold set for eliminating a noise or the like. Thus, the surface of an object such as an organ is extracted accurately with incorrect extraction due to a noise prevented. The thus obtained points are synthesized to form the surface of the object, whereby a three-dimensional image depicting the object can be displayed accurately.

The operation of the ultrasonic viewer 2 will be described below.

For ultrasonic viewing, the insertional part 4a of the ultrasonic probe 4 is inserted into a body cavity. Under the control of the system controller 12, the transmitter receiver 6 and driver 5 drives the ultrasonic transducer 4b in the ultrasonic probe 4 in a spiral form. Ultrasonic waves are thus transmitted to a living body, and echoes are received from the living body. Consequently, data provided by the echoes emanating from a three-dimensional area in a body cavity is acquired.

Specifically, the motor 5b incorporated in the driver 5 in the ultrasonic probe 4 is rotated in order to drive and rotate the ultrasonic transducer 4b attached to the tip of the shaft 4c. Ultrasonic waves are then transmitted radially in a direction perpendicular to the axis of the ultrasonic probe 4 (vertical direction in FIG. 1), and echoes or reflected ultrasonic waves having undergone changes in acoustic impedance are received.

With the rotation, a three-dimensional area is scanned linearly along the axis of rotation at intervals of a pitch of the male thread 4d (that is, spiral scanning). Thus, echoes emanating from the three-dimensional area are acquired. The echoes are converted into digital signals by the A/D converter 7 via the slip ring 5d in the driver 5, thus providing data.

The data provided by the echoes, that is, echo data is stored in the frame memory 8, and displayed in real time (ultrasonic view image) on the monitor 11 via the DSC 9 and D/A converter 10. At the same time, the acquired data is sent as one-dimensional echo data (data of consecutive sound rays) in the form of a digital signal from the output stage of the A/D converter 7 to the image processing unit 3. At this time, associated data such as the size of a two-dimensional image data and a distance between images is also sent to the image processing unit 3.

Next, the operation of the image processing unit 3 will be described.

Data of sound rays acquired from a body cavity by the ultrasonic probe 4 through spiral scanning and sent from the ultrasonic viewer 2 to the image processing unit 3 is converted into image data by the polar coordinate transformation unit 16. In the image data memory 17, the image data is written as a plurality of consecutive two-dimensional images together with the associated data in the order in which the images are acquired.

The image data memory 17 functions as a three-dimensional echo data memory. The image processor 18 performs image processing such as surface point extraction, shading, synthesis, and coordinate transformation on the image data and associated data stored in the image data memory 17.

The processed image data is then sent to the frame buffer 22, temporarily stored therein, and then sent to the three-dimensional image processing monitor 24 via the D/A converter 23. Thereafter, a three-dimensional image based on the echo data is displayed on the three-dimensional image processing monitor 24.

The steps of various kinds of image processing to be performed by the image processor 18 are controlled by the CPU 13.

The details of image processing performed by the CPU 13 and image processor 18 will be described with reference to the flowchart of FIG. 2 and the explanatory diagrams concerning processing steps of FIGS. 3 to 16.

Figure 2:
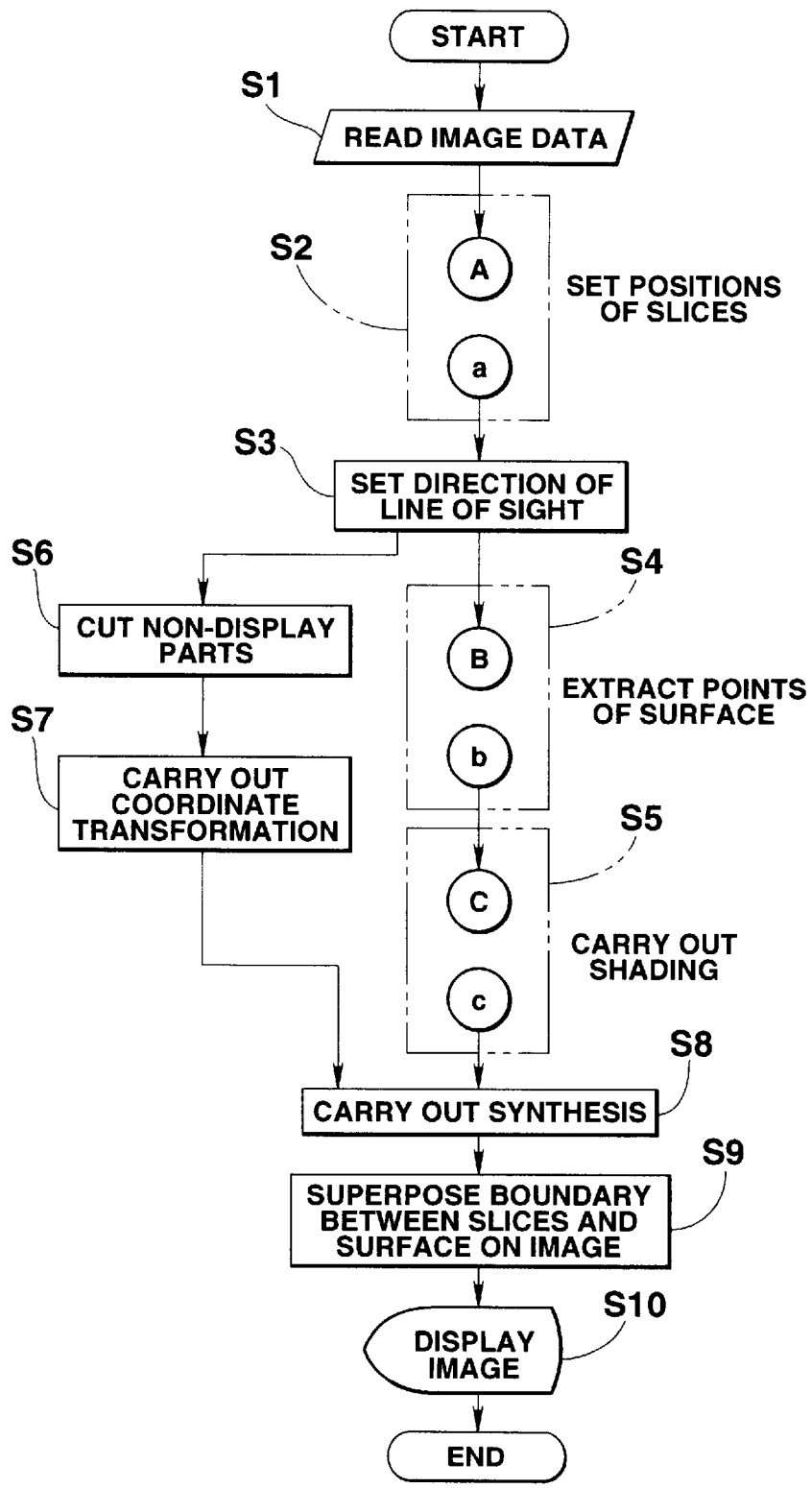

At step S1 in FIG. 2, image data of a three-dimensional area is read together with associated data from the image data memory 17. At step S2 in FIG. 2, the positions of slices are specified.

The details of step S2 will be mentioned below.

Figure 3:
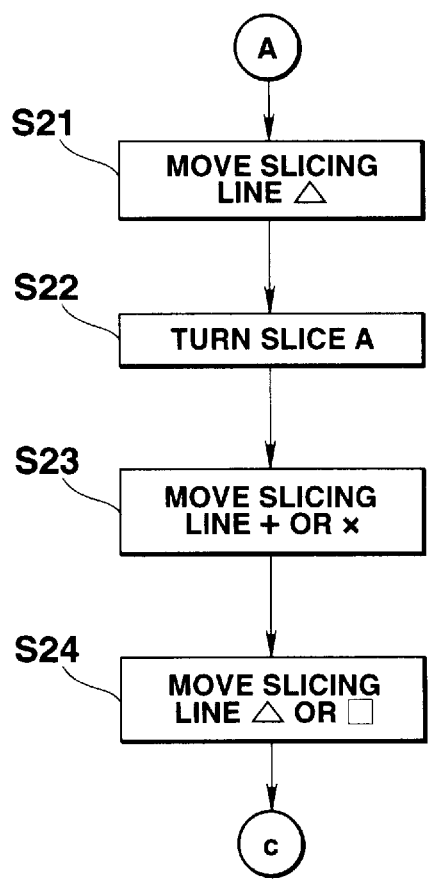
Figure 4:
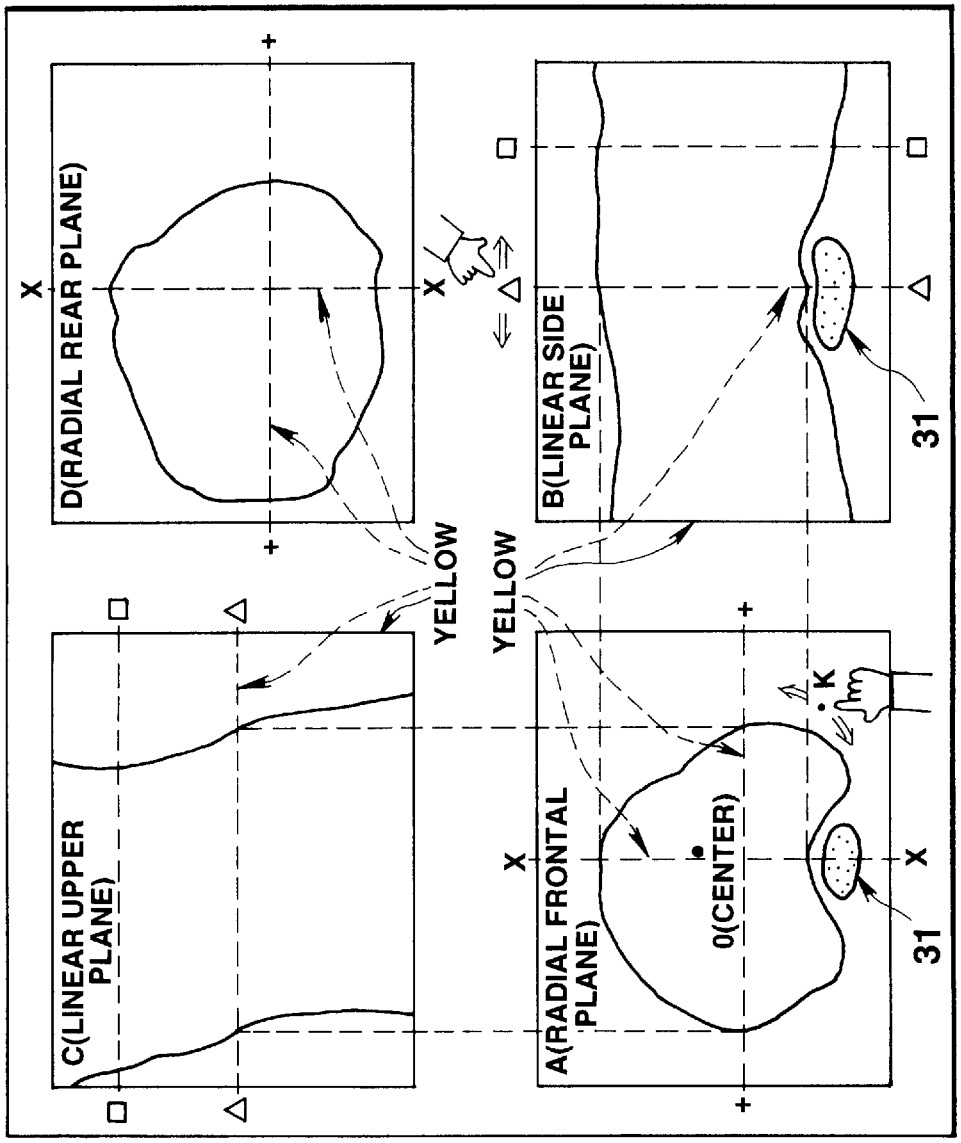

FIG. 3 is a flowchart describing the contents of an exemplary example of step S2. FIG. 4 shows a plurality of tomographic images, or specifically, four tomographic images (echo data of slices) constructed by a tomographic image constructing means for the purpose of constructing a three-dimensional image on the three-dimensional image processing monitor 24. An area indicated with small dots in FIG. 4 is a region of interest 31 such as a lesion.

Figure 16:
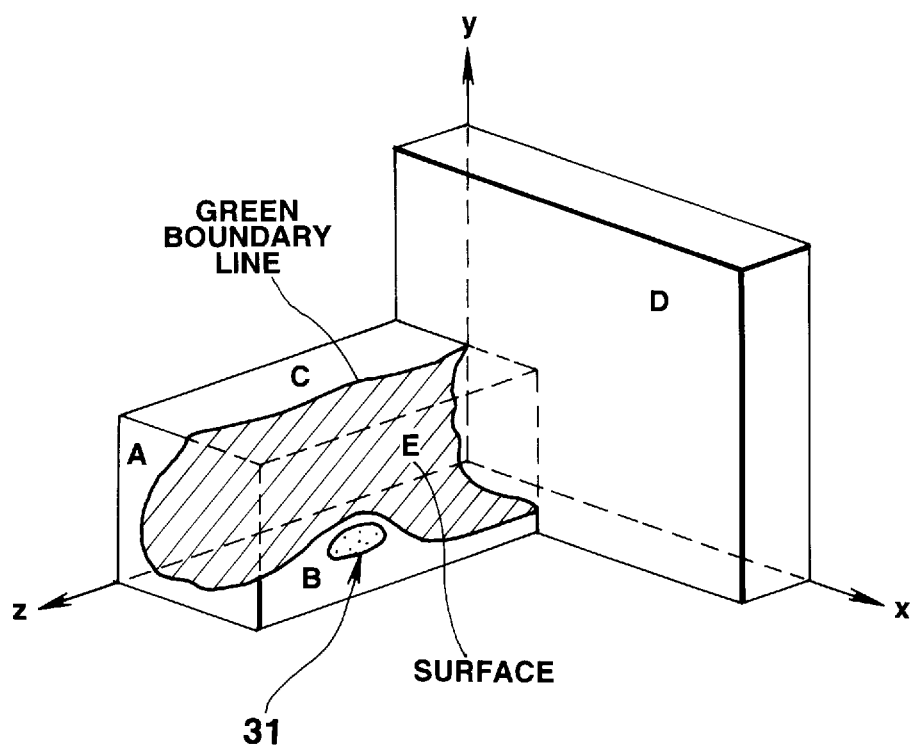

At step S1, image data read from the image data memory 17 is used to display the tomographic images on the three-dimensional image processing monitor 24. FIG. 16 shows a three-dimensional image constructed finally by properly setting the four tomographic images. Slices A, B, C, and D shown in FIG. 4 correspond to slices A, B, C, and D shown in FIG. 16 (in reality, the slices shown in FIG. 4 including slice A which correspond to the slices in FIG. 16 have undergone a parallel movement or rotation so that a lesion is contained).

Specifically, slice C is perpendicular to slices A and D, and contains a slicing line + shown in FIG. 4. Slice B contains a slicing line × shown in FIG. 4. Slice A is perpendicular to slices B and C and contains a slicing line Δ shown in FIG. 4. Slice D contains a slicing line □ shown in FIG. 4.

In FIG. 16, a z axis is defined along the axis of the inserted ultrasonic probe 4 (longitudinal direction of the ultrasonic probe 4) as mentioned later. The description will proceed on the assumption that slices A and D perpendicular to the z axis and parallel to each other are regarded as radial planes, and slices B and C parallel to the z axis are regarded as linear planes. In this case,. slice A shall be termed as a radial frontal plane meaning a frontal plane to be scanned by radial scanning, while slice D shall be termed as a radial rear plane meaning a rear plane to be scanned by radial scanning. As shown in FIG. 16, a y axis is defined upward. In compliance with a three-dimensional space, slice B shall be termed as a linear side plane and slice C shall be termed as a linear upper plane.

The slicing lines indicated with dashed lines in FIG. 4 and the contour of a slice being handled are colored in yellow or the like so that they can be distinguished readily from tomographic images displayed in black-and-white gray scale.

At step S21 in FIG. 3, a user touches a Δ cursor in slice B (linear side plane) in FIG. 4 on the touch panel 25 with his/her finger, and slides the Δ cursor in a direction of an arrow (lateral direction in FIG. 4) so that the region of interest 31 such as a lesion can appear in slice A. This causes the slicing line Δ to move responsively. The region of interest 31 then appears in slice A (radial frontal plane) defined by the slicing line Δ.

Thus, a tomographic image constructing means or tomographic image construction facility includes a slicing line moving means or slicing line movement facility for moving slicing lines indicating the positions of slices.

At step S22 in FIG. 3, the user turns slice A so that the region of interest 31 will be oriented properly. Specifically, the user touches point K in slice A in FIG. 4 with his/her finger, and moves his/her finger in a direction of an arrow. This causes the whole of slice A to turn in the direction of an arrow with center point O of slice A as a center. The region of interest 31 comes immediately below an object in slice A shown in FIG. 4. Thus, a tomographic image turning means or tomographic image turning facility is included.

At step S23 in FIG. 3, the slicing line + or × is moved so that the slicing line + or × traverses the region of interest 31. The way of the movement is identical to the way of moving the Δ cursor. The region of interest 31 then appears in slice B or C. In FIG. 4, the slicing line x has been moved.

At step S24 in FIG. 3, the slicing lines Δ and □ are moved so that the region of interest 31 will be interposed between the slicing lines.

Thus, setting the positions of slices for constructing a three-dimensional image shown in FIG. 16 has been completed.

As mentioned above, in a specified one of a plurality of tomographic images depicting differently oriented slices, which have been constructed by the tomographic image constructing means (facility), the slicing line moving means moves a slicing line indicating the position of a slice, and the tomographic image turning means turns a tomographic image. The tomographic images other than the specified one are then modified accordingly. At whatever position in a tomographic image a lesion resides, a slice can be set so that the slice passes through the lesion. Consequently, the depth or the like of the lesion can be assessed.

Figure 5:
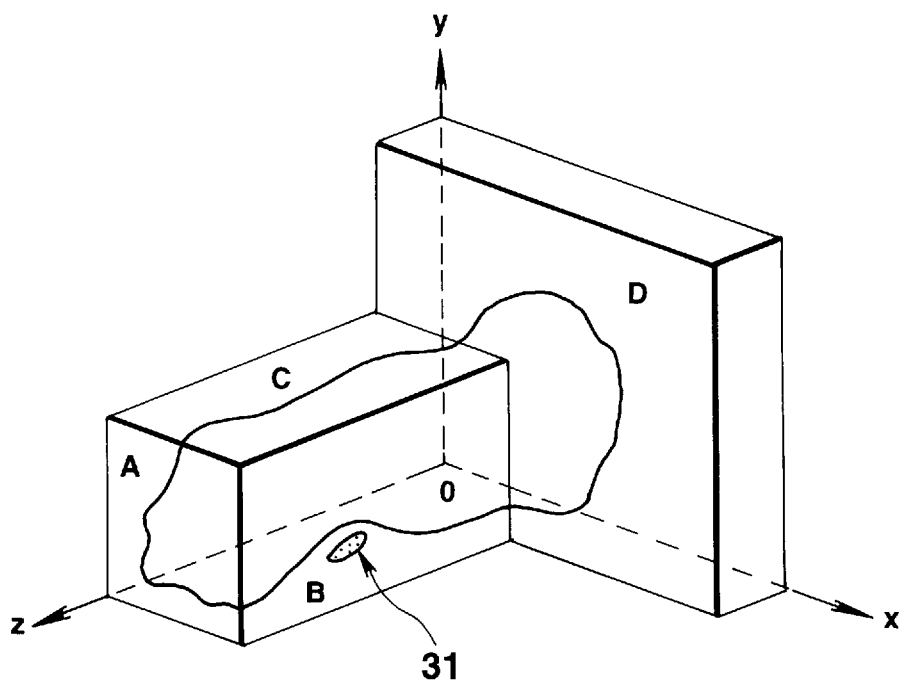

After slice position setting of step S2 is completed, when the user presses the simple three-dimensional image construction key 21b, a simple three-dimensional image not having undergone surface point extraction is constructed as shown in FIG. 5 for the user's information, and then displayed on the three-dimensional image processing monitor 24.

A masking means or display form designating means is included for setting or displaying slices so that the relationship of correspondence between part of each tomographic image used to construct a three-dimensional image and the other part thereof unused thereto can be grasped readily.

Figure 6:
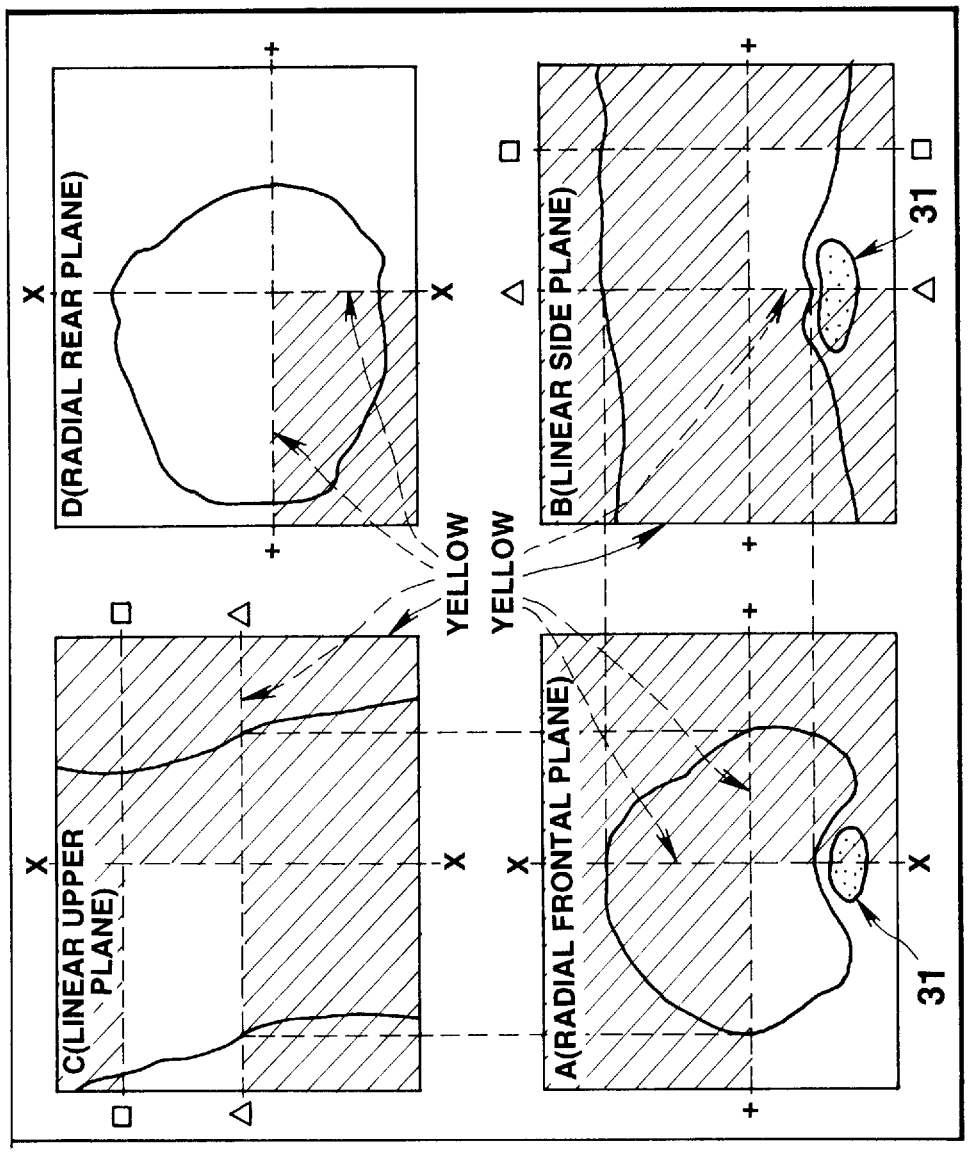

In FIG. 6, parts of the tomographic images shown in FIG. 4 which are not used to construct the simple three-dimensional image shown in FIG. 5 are hatched. When the user presses the mask switching key 21a on the operation terminal 21, the hatched parts are made dimmer than the other parts so that the relationship of correspondence between the three-dimensional oblique display shown in FIG. 5 and corresponding parts of the tomographic images or the relationship of correspondence among the parts of the tomographic images can be grasped readily. When the mask switching key 21a is pressed again, the original display shown in FIG. 4 reappears. It is also possible to carry out the aforesaid steps S21 to S24 with the hatched parts held dim.

As mentioned above, a display form designating means is included: that is, when the mask switching key 21a is handled to designate or select a display form, it can be designated whether echo data to be synthesized to construct a three-dimensional image and the other echo data (echo data actually unused to construct the three-dimensional image) are displayed in different forms or in the same form.

At step S3 in FIG. 2, the direction of a line of sight is specified.

Step S3 will be described below.

Figure 7:
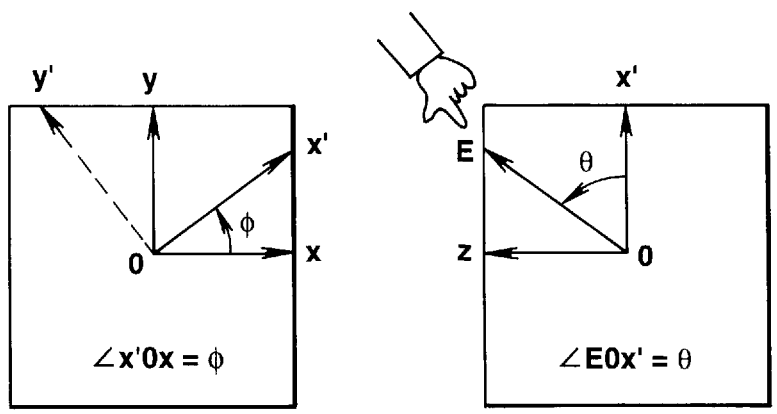
Figure 8:
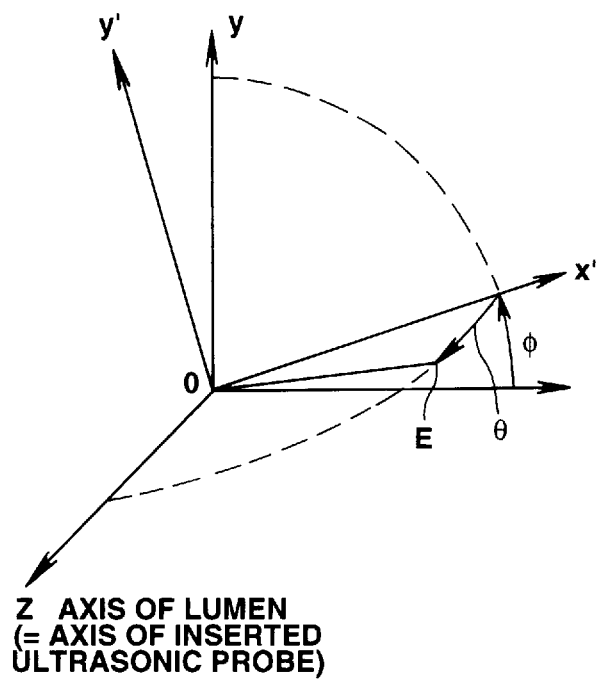

At step S3, current set values concerning the direction of a line of sight are displayed in sub screens for setting shown in FIG. 7 on the three-dimensional image processing monitor 24. FIG. 8 is a diagram for explaining the spatial relationship between angles Θ and φ shown in FIG. 7. Coordinate axes Ox, Oy, and Oz are defined in image data. The z axis coincides with the direction of the axis of a lumen in a living body.

In this embodiment, the ultrasonic probe 4 is inserted into a body cavity along the axis of a lumen in a living body. The z axis is therefore defined in the direction of the axis of the inserted ultrasonic probe 4. In this embodiment, the angles Θ and φ are set to 45° by default so that the inside of a body cavity can be expressed stereoscopically from an oblique direction even when setting is not particularly modified.

The user touches point E in the sub screen on the touch panel 25 so as to change the direction of a line of sight to a desired direction, and slides point E in a circumferential direction with respect to center O of the sub screen. This causes segment OE to move. The angle Θ of a line of sight is modified and set accordingly. Thus, the polar coordinate transformation unit 16 serving as a coordinate transforming means transforms polar coordinates. The same applies to the angle φ, though a point to be touched with a finger is point x'.

The display shown in FIG. 8 is also displayed on the three-dimensional image processing monitor 24 responsively to the display of the sub screens for setting shown in FIG. 7. The direction of a line of sight in which a three-dimensional shown in FIG. 16 is viewed is thus set.

As mentioned above, in this embodiment, the coordinate transforming means transforms coordinates of echo data of slices and echo data of a surface, and the line-of-sight angle setting means sets angles defining a line of sight or the direction of the line of sight, in which a three-dimensional image is viewed, as angles in a coordinate system having the axis of a lumen in a living body or the axis of an inserted ultrasonic probe as one of the coordinate axes. The display means displays the angles defining a line of sight in the coordinate system having the axis of a lumen in a living body or the axis of an inserted ultrasonic probe as one of the coordinate axes. Thus, the angles defining a line of sight in which a three-dimensional image is viewed can be set easily, and the line of sight can be understood intuitively and anatomically easily.

At step S4 in FIG. 2, points defining the surface of an object such as an organ are extracted. The details of step S4 will be explained below.

Figure 9:
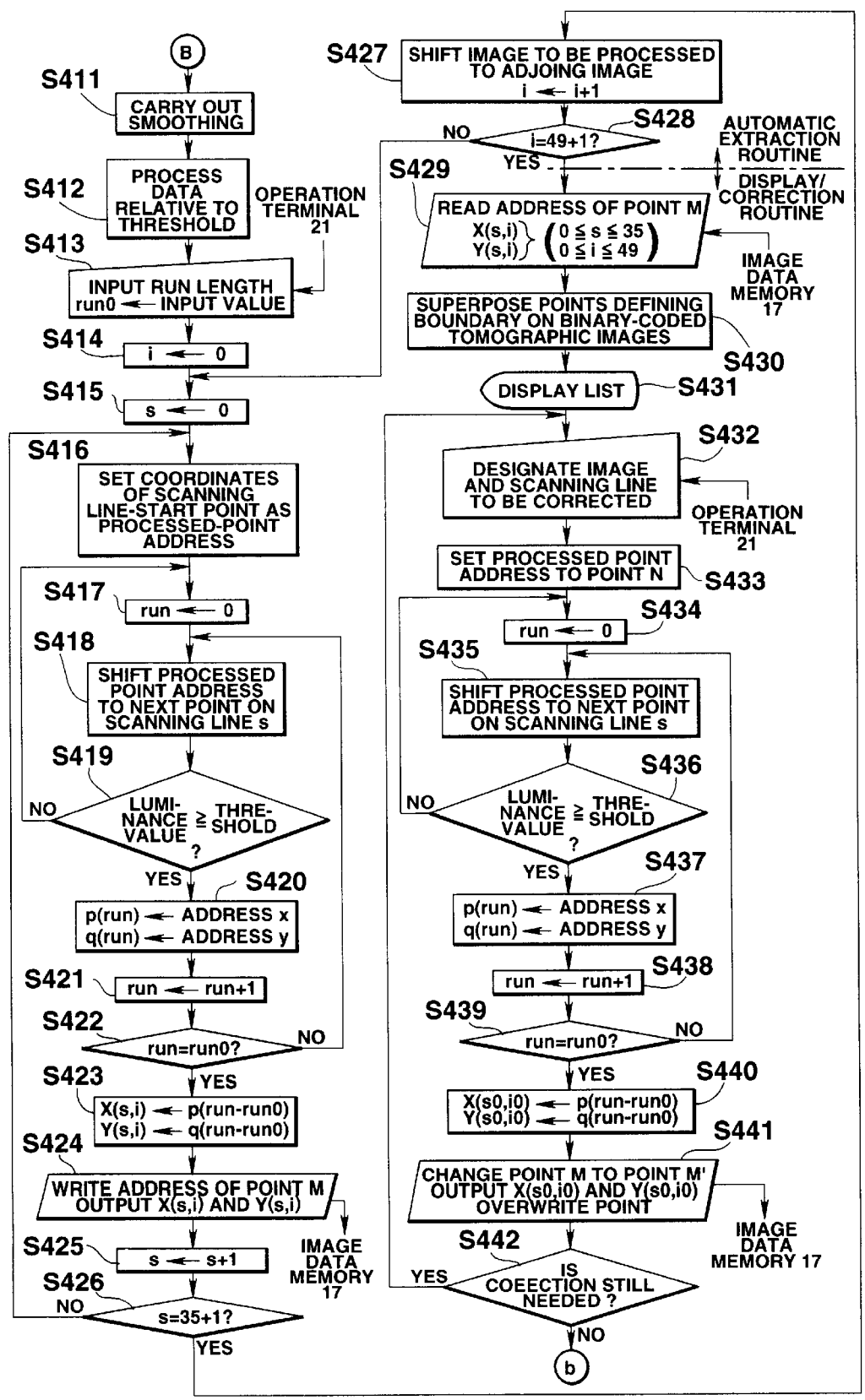
Figure 10:
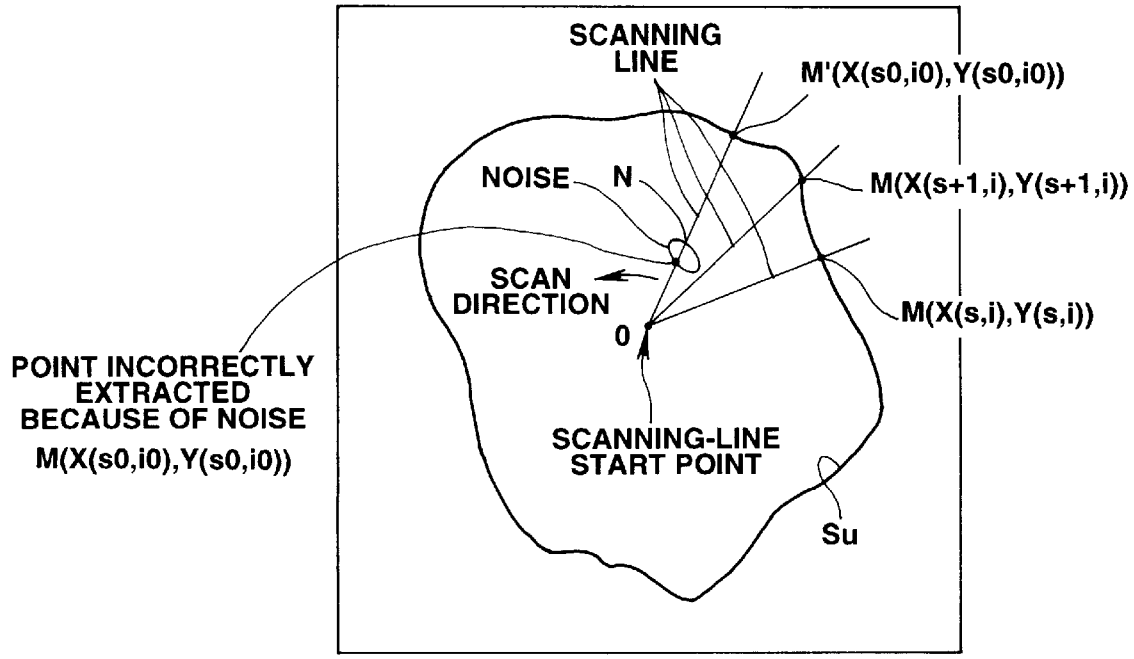

FIG. 9 is a flowchart describing the contents of step S4. FIG. 10 is a diagram for explaining scanning intended to extract points defining the surface Su of an object and started with start point O of scanning lines. FIG. 10 illustrates the operation to be exerted when image data is scanned along each scanning line from start point O of scanning lines to a far point, and a point closest to start point O of scanning lines is extracted from each run of consecutive points, at which data values exceed a threshold set for surface extraction, having a length larger than a given length.

In FIG. 10, luminance values at the points along a scanning line inside the surface Su except those included in a noise are small, while luminance values at the points along the scanning line outside the surface Su are large. Thus, an extracting means for extracting the surface Su of an object by extracting points as mentioned above can be realized.

Steps S411 to S428 constitute an automatic extraction routine for automatically extracting points defining a surface, and steps S429 to S442 constitute a display/correction routine for displaying and correcting an automatically detected boundary.

The contents of the automatic extraction routine will be described below. The automatic extraction routine involves a run extracting means for extracting points defining a surface from runs of points.

At step S411 in FIG. 9, image data is smoothed. The unit of smoothing is varied optimally relative to the ultrasonic resolution attainable during scanning by the ultrasonic transducer in the ultrasonic probe 4.

At step S412 in FIG. 9, image data is processed relative to a threshold set for surface extraction. Luminance values at points equal to or smaller than the threshold are replaced with Os. The threshold can be varied at the operation terminal 21.

At step S413 in FIG. 9, a threshold of a length of a run of points at which luminance values exceed the threshold, which is set to regard a run of points whose length is equal to or smaller than the threshold as a noise, is assigned to variable runO. This entry is achieved at the operation terminal 21.

The operation terminal 21 serves as a noise elimination setting means used to eliminate a run of consecutive points, at which data values exceed a threshold, having a length equal to or smaller than a set length as a noise. The image processor 18 eliminates a run of consecutive points, at which data values exceed a threshold, having a length equal to or smaller than the threshold or the set length as a noise.

Thus, as shown in FIG. 10, the surface Su of an object is extracted with incorrect detection suppressed. In FIG. 10, an incorrect point detected because of a noise is shown for a better understanding of the operation of the correction routine.

The threshold of the length can be varied at the operation terminal 21. For example, even when a noise is, as shown in FIG. 10, present, if the threshold is set to a value larger than the length of the noise, the noise can be eliminated.

At step S414 in FIG. 9, O is assigned to variable i. Variable i indicates the number of a two-dimensional image that should be processed at present among a plurality of consecutive two-dimensional images written as image data in the image data memory 17 (the term image i may be used). In this embodiment, since all the 50 consecutive two-dimensional images shall be processed, the following relationship is established:

$$0 \leq i \leq 49$$

Incidentally, the present invention is not limited to the procedure of processing all images but can also apply to the procedure of processing a specified image alone.

At step S415 in FIG. 9, 0 is assigned to variable s. Variable s indicates a scanning line that should be processed at present among scanning lines extending from a start point of scanning lines to far points (the term scanning line s may be used). In this embodiment, since 36 scanning lines are traced radially at intervals of, for example, 10°, the following relationship is established:

$$0 \leq s \leq 35$$

When the interval is adopted, an extracted boundary is composed of points. When the interval is made smaller, the extracted boundary is defined substantially linearly. This embodiment covers extraction of such a linearly defined boundary.

At step S416 in FIG. 9, the coordinates of the start point of scanning lines are set as a processed-point address. The processed-point address is defined with addresses x and y that correspond to the x and y coordinates of a point currently being processed. In this embodiment, the start point of scanning lines is defined in the center of each two-dimensional image. In FIG. 10, the start point is point 0.

At step S417 in FIG. 9, 0 is assigned to variable run. Variable run is used to measure the length of a run.

At step S418 in FIG. 9, the processed-point address is shifted to the next point along scanning line s.

At step S419 in FIG. 9, it is judged whether a luminance value at the point indicated with the processed-point address is larger or smaller than the threshold value relative to which image data is processed. If the luminance value is larger, control is passed to step S420. If the luminance value is smaller, control is jumped to step S417.

At step S420 in FIG. 9, address x of the processed-point address is assigned to the run-th variable p(run) of one-dimensional array variables p. Address y of the processed-point address is assigned to the run-th variable q(run) of one-dimensional array variables q.

At step S421 in FIG. 9, 1 is added to variable run.

At step S422 in FIG. 9, it is judged whether or not variable run agrees with runO. If the values agree with each other, control is passed to step S423. If the values disagree with each other, control is jumped to step S418.

At step S423 in FIG. 9, p(run-runO) is assigned to two-dimensional array variable X(s, i), and q(run-runO) is assigned to two-dimensional array variable Y(x, i). Thus, a point closest to the start point of scanning lines is extracted as coordinates (X(x, i), Y(s, i)) from a run of consecutive points, at which luminance values exceed the threshold, having a length larger than runO.

At step S424 in FIG. 9, values X(s, i) and Y(s, i) are output to the image data memory 17. In other words, at step 424, the address of point M in FIG. 10 is written in the image data memory 17.

At step S425 in FIG. 9, 1 is added to variable s. In other words, the scanning line to be processed is shifted to an adjoining one.

At step S426 in FIG. 9, it is judged whether or not variable s agrees with 35+1. In other words, it is judged whether or not processing the last scanning line in the two-dimensional image i has been completed. If the values agree with each other, control is passed to step S427. If the values disagree with each other, control is jumped to step S416.

At step S427 in FIG. 9, 1 is added to variable i. In other words, the two-dimensional image to be processed is shifted to an adjoining two-dimensional image.

At step S428 in FIG. 9, it is judged whether or not variable i agrees with 49+1. In other words, it is judged whether or not processing the last two-dimensional image among the two-dimensional images written in the image data memory 17 has been completed. If the values agree with each other, control is passed to step S429. If the values disagree with each other, control is jumped to step S415.

Thus, within the automatic extraction routine, the coordinates of points recognized to define the surface of a body cavity, that is, a boundary are written in the image data memory 17 by processing all the scanning lines in all the two-dimensional images.

The automatic extraction routine is effective in substantially nullifying incorrect extraction of a surface caused by a noise or the like. In this embodiment, a boundary correcting means or boundary correction facility for correcting an incorrectly-extracted boundary that cannot be excluded by the automatic extraction routine is included, and a display/correction routine for displaying a corrected boundary is included.

The boundary correction facility corrects points defining the surface of an object. Points defining the surface of an object, which have been extracted improperly, can therefore be corrected. Incorrect extraction of a noise or the like can thus be reduced further. Eventually, a three-dimensional image can be displayed accurately.

The display/correction routine will be described below.

At step S429 in FIG. 9, values X(s, i) and Y(s, i) are read relative to all the values of integers i and s in the ranges of $0 \leq i \leq 49$ and $0 \leq s \leq 35$. That is to say, the coordinates of points recognized to define a boundary are read from the image data memory 17.

At step S430 in FIG. 9, points whose coordinates correspond to coordinates ((X(s, i), Y(s, i)) are superposed on each two-dimensional image that has been processed relative to the threshold. That is to say, a boundary superposing means or boundary superposition facility is included for checking if surface point extraction has been carried out properly. The boundary superposition facility superposes coordinates (X(s, i), Y(s, i)), which define an extracted surface, in the form of points on each two-dimensional image.

At step S431 in FIG. 9, the two-dimensional images on which the points defining a boundary are superposed are listed on the three-dimensional image processing monitor 24.

At step S432 in FIG. 9, two-dimensional image iO to be corrected and scanning line sO to be corrected are designated.

In FIG. 10, a point on scanning line sO is specified as point M(X(sO, iO), Y(sO, iO)). The point is a point incorrectly extracted because of a residue in a body cavity or a noise and located inward of a point that should have been extracted with respect to start point O of scanning lines. For designation, a point near the scanning line on the touch panel 25 is touched with a finger. In FIG. 10, both i and iO coexist because the image iO to be corrected is referred to as one of general images i (in FIG. 10, image iO corresponds to image i, and scanning line sO corresponds to scanning line s+2).

At step S433 in FIG. 9, the coordinates of a far end point of a run including point M(X(sO, iO), Y(sO, iO)) along scanning line sO are set as the processed-point address. In FIG. 10, the point is point N.

Steps S434 to S439 in FIG. 9 are basically identical to steps S417 to S422. The description of the steps will therefore be omitted.

At step S440 in FIG. 9, p(run-runO) is assigned to two-dimensional array variable X(sO, iO), and q(run-runO) is assigned to two-dimensional array variable Y(sO, iO). The coordinates of a point second closest to the start point of scanning lines secondly to the extracted point are extracted as X(sO, iO) and Y(sO, iO). In FIG. 10, the point is point M'(X(sO, iO), Y(sO, iO)).

At step S441 in FIG. 9, the values X(sO, iO) and Y(sO, iO) are output to the image data memory 17 and overwritten on stored data. In other words, point M(X(sO, iO), Y(sO, iO)) in FIG. 10 is changed to point M'(X(sO, iO), Y(sO, iO)), and thus point M(X(sO, iO), Y(sO, iO)) incorrectly extracted because of a noise or the like is corrected.

At step S442 in FIG. 9, a message asking if correction is still needed is output to the three-dimensional image processing monitor 24. The user makes a response at the operation terminal 21. If correction is needed, control is jumped to step S432. If correction is not needed any longer, control is passed to step S5 in FIG. 2.

Thus, the display/correction routine corrects points incorrectly extracted because of a residue in a body cavity or a noise.

At step S5 in FIG. 2, a surface extracted at step S4 is shaded.

The contents of the processing of step S5 will be described below.

Figure 12:
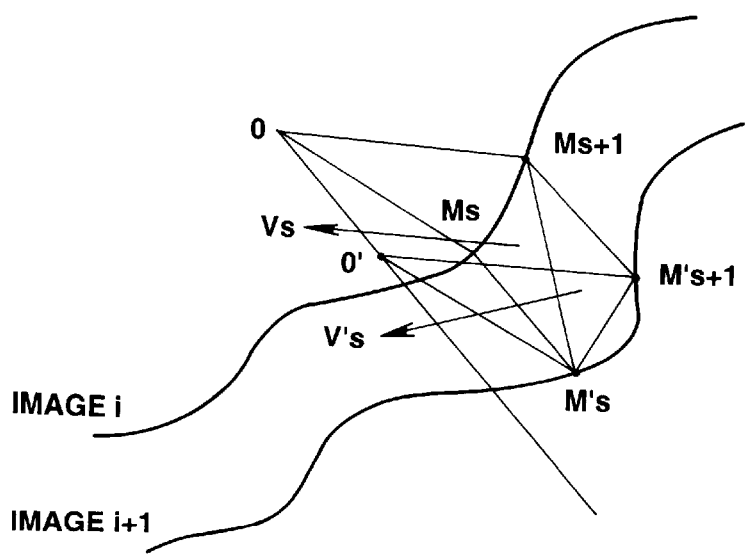
Figure 11:
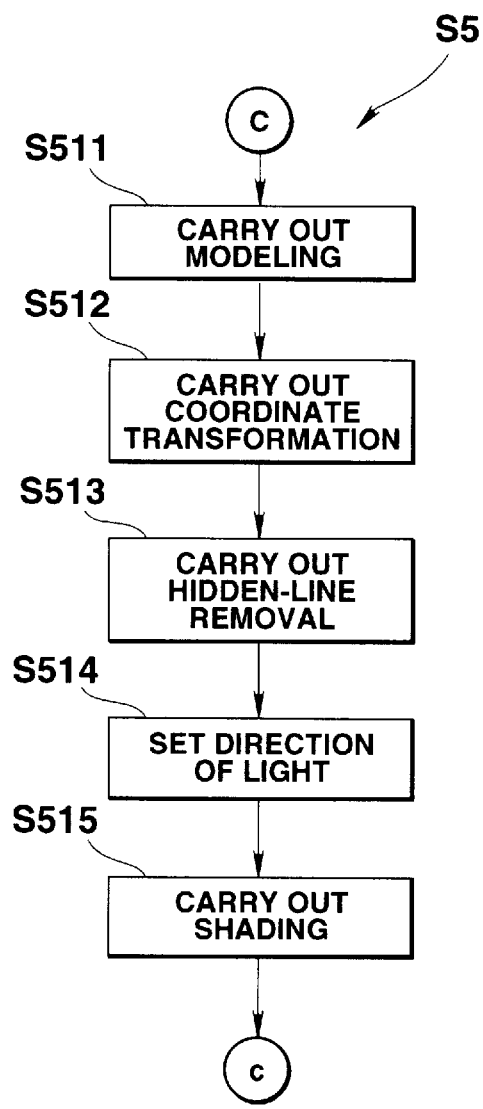

FIG. 11 is a flowchart describing the contents of the processing of step S5. FIG. 12 is a diagram for explaining the processing of shading.

At step S511 in FIG. 11, image data is modeled. In this embodiment, a plurality of polygons are hypothetically drawn using points extracted to define a boundary (surface of a body cavity) at step S4.

FIG. 12 shows two of the polygons, that is, two triangles having vertices Ms, Ms+1, M's, and M's+1, that is, $\Delta$MsMs+1M's and $\Delta$Ms+1M'sM's+1. Start point O of scanning lines, and points Ms and Ms+1 are points in two-dimensional image i, while start point O' of scanning lines, and points M's and M's+1 are points in two-dimensional image i+1. Scanning lines having the points Ms and M's respectively and scanning lines having the points Ms+1 and M's+1 respectively have the same numbers. The coordinates of the four points are as follows:

Ms:
(X(s, i), Y(s, i))
Ms+1: (X(s+1, i), Y(s+1, i))
M's: (X(s, i+1), Y(s, i+1))
M's+1: (X(s+1, i+1), Y(s+1, i+1))

At step S511, a normal vector of each polygon is calculated using the coordinates of vertices. In FIG. 12, normal vectors of the polygons are vectors Vs and V's.

At step S512 in FIG. 11, the coordinates of the vertices of each polygon are transformed according to the direction of a line of sight set at step S3. At this time, a normal vector of each polygon is also calculated.

At step S513 in FIG. 11, each polygon is subjected to hidden-line removal. Specifically, lines hidden behind a polygon are removed.

At step S514 in FIG. 11, the direction of light is set. That is to say, a light angle setting means or light angle setting facility is included for setting the direction of light (angles defining light).

Figure 13:
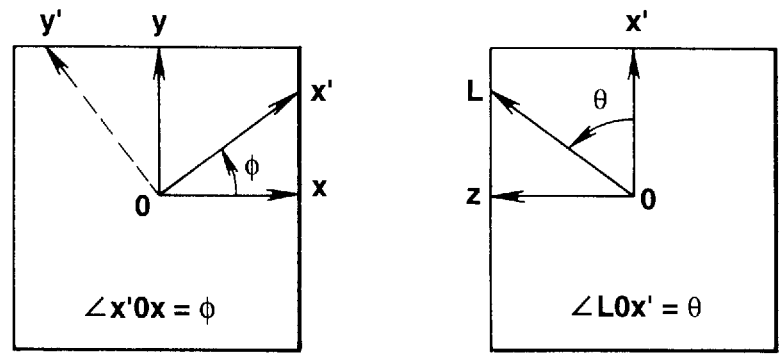

At step S514, current set values defining the direction of light are displayed in the sub screens for setting shown in FIG. 13 on the three-dimensional image processing monitor 24.

Figure 14:
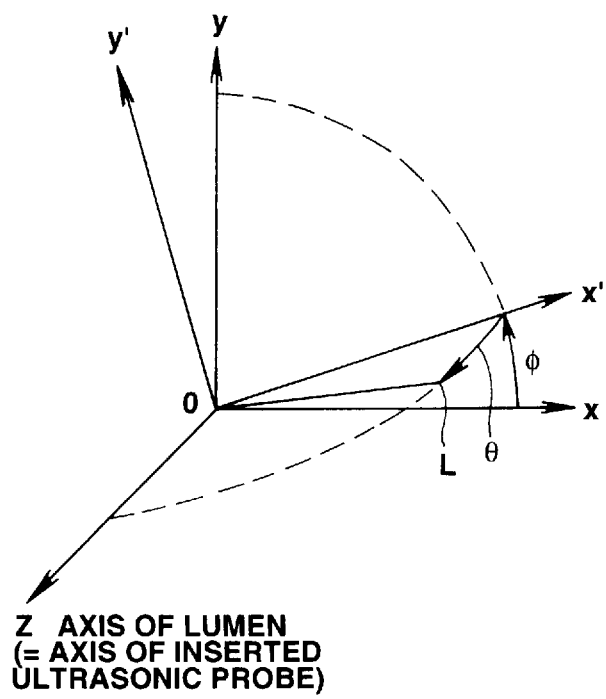

FIG. 14 is a diagram for explaining the spatial relationship between angles $\Theta$ and $\phi$ shown in FIG. 13. The display shown in FIG. 14 is also displayed in the sub screen for setting on the three-dimensional image processing monitor 24 responsively to the display of the sub screens for setting shown in FIG. 13. The setting procedure or the like is identical to that for step S3. The description of the procedure will therefore be omitted.

In this embodiment, the light angle setting means sets angles defining light used for shading as angles in a coordinate system having the axis of a lumen in a living body or the axis of an inserted ultrasonic probe as one of the coordinate axes thereof. The display means displays the angles defining light in the coordinate system having the axis of a lumen in a living body or the axis of an inserted ultrasonic probe as one of the coordinate axes thereof. Thus, the surface of a desired object can be expressed stereoscopically, and the angles defining light can be set for an intuitively and anatomically better understanding.

At step S515 in FIG. 11, based on the distance of each polygon from an observing point or angles between the normal vector of the polygon and the direction of light set at step S514, an algorithm describing shading such as flat shading, glow shading, phone shading, or depth shading is used to determine the brightness levels of points within each polygon.

Thus, a surface is shaded.

Figure 15:
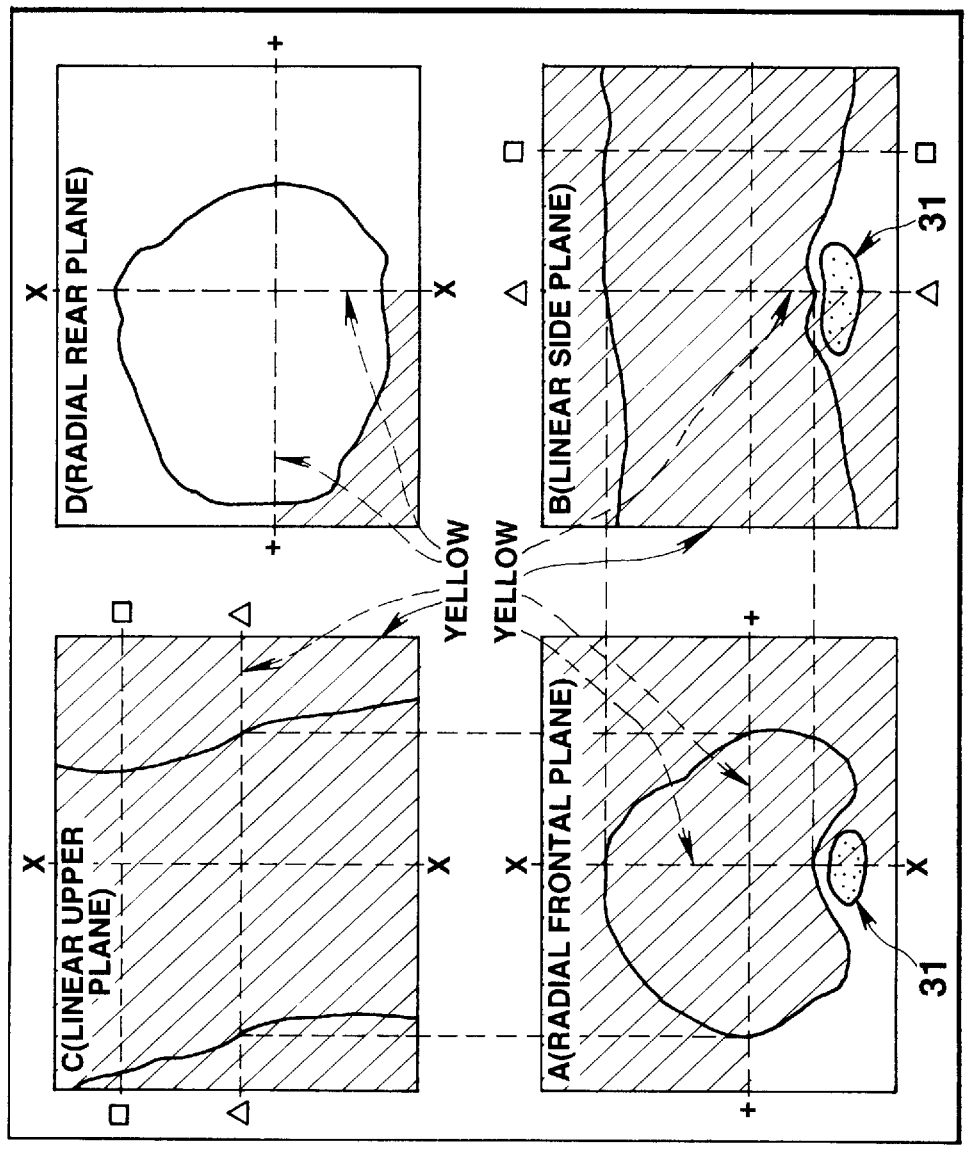

At step S6 in FIG. 2, non-display parts of slices whose positions are set at step S2 are cut out. In FIG. 15, hatched areas correspond to non-display parts of four slices to be used to construct a three-dimensional image shown in FIG. 16. The data of the parts is deleted.

At step S7 in FIG. 2, the remaining display parts of the four slices to be used to construct a three-dimensional image, that is, parts remaining intact as a result of step S6 are subjected to coordinate transformation.

At step S8 in FIG. 2, synthesis is carried out. Specifically, a surface whose defining points are extracted at step S4 and which is shaded at step S5 is synthesized with slices whose non-display parts are cut out and which have undergone coordinate transformation, whereby the three-dimensional image shown in FIG. 16 is constructed. In FIG. 16, the surface is denoted with E.

At step S9 in FIG. 2, a green line is superposed on the three-dimensional image as a boundary line between the slices and surface.

That is to say, in this embodiment, a slice-surface boundary superposing means for superposing a boundary line between slices and a surface on a three-dimensional image is included. The slice-surface boundary superposing means superposes a boundary line between data of slices and data of a surface as a slice-surface boundary line on a three-dimensional image. The display means displays the three-dimensional image on which the slice-surface boundary line is superposed. Thus, the surface can be distinguished readily.

At step S10 in FIG. 2, a constructed three-dimensional image shown in FIG. 8 is displayed on the three-dimensional image processing monitor 24.

As mentioned above, the CPU 13 and image processor 18 function as a surface point extracting means, shading means, synthesizing means, run extracting means, boundary superposing means, tomographic image constructing means, coordinate transforming means, and slice-surface boundary superposing means. In FIG. 1, the image processor 18 alone is shown to include all these facilities for convenience' sake.

The touch panel 25 functions as a slice point setting means, boundary correcting means, corrected scanning line designating means, slicing line moving means, tomographic image turning means, masking means, light angle setting means, and line-of-sight angle setting means.

The mask switching key 21a functions as a display form designating means.

The image data memory 17 functions as a three-dimensional echo data memory means.

The three-dimensional image processing monitor 24 functions as a display means.

This embodiment has the advantages set forth below.

In this embodiment, the run extracting means scans data along each scanning line toward a far point, and extracts a point closest to a start point of scanning lines from each run of consecutive points, at which luminance values exceed a certain threshold, having a length larger than a given length. A run of points whose length is equal to or smaller than the given length can be eliminated as a noise. The surface of a desired object can be expressed accurately without any interference of a noise or the like.

In this embodiment, at step S413, a length is input so that a run of points whose length is equal to or smaller than the length can be recognized as a noise. Various kinds of noise elimination can therefore be carried out.

If a point should be extracted incorrectly because of a noise or the like, an extracted boundary can be corrected by the boundary correction facility. The surface of an object can therefore be extracted with little influence of a noise or the like.

In this embodiment, since the image shown in FIG. 10 can be referenced, a boundary can be corrected while it is checked whether or not correction is made properly.

Specifically, extracted points defining the surface of an object are superposed as a boundary on all of a plurality of consecutive tomographic images or on a specified tomographic image by the boundary superposition facility. Resultant images are then displayed by the display means. It can therefore be checked if the surface of an object is extracted properly.

In this embodiment, when the simple three-dimensional image construction key 21b is pressed, a simple three-dimensional image not having undergone surface point extraction is displayed as shown in FIG. 5 for user's information. The imagery of a completed three-dimensional image can be depicted readily.

Moreover, the slicing line moving means moves a slicing line indicating the position of a slice in a specified tomographic image among a plurality of tomographic images depicting differently-oriented slices which are constructed by the tomographic image constructing means. The tomographic image turning means turns a tomographic image. The other tomographic images other than the specified tomographic image are then modified accordingly. At whichever position in a tomographic image a lesion resides, a slice can be specified so that the slice contains the lesion. The depth of the lesion can be assessed.

Moreover, the tomographic image constructing means constructs a plurality of tomographic images depicting differently-oriented slices, which are produced using data provided from a three-dimensional area. The slicing line moving means moves a slicing line indicating the position of a slice in the plurality of constructed tomographic images. The masking means can display echo data used to construct a three-dimensional image and the other echo data in different forms. Consequently, parts of tomographic images used to construct a three-dimensional image and the other parts can be distinguished from each other, and the relationship of correspondence between the parts can be grasped readily.

Moreover, a display form designating means is included for designating either of two kinds of display forms; a display form for displaying normal tomographic images, and a display form for displaying echo data used to construct a three-dimensional image and the other echo data in different forms for efficient setting of slices. If a mask is annoying, the mask is removed, and any of a plurality of tomographic images depicting slices can be used for ordinary diagnosis.

In this embodiment, the light angle setting means sets angles defining light used for shading as angles in a coordinate system having the axis of a lumen in a living body or the axis of an inserted ultrasonic probe as one of its coordinate axes. The display means displays the angles defining light in the coordinate system having the axis of a lumen in a living body or the axis of an inserted ultrasonic probe as one of its coordinate axes. Consequently, the surface of a desired object can be expressed stereoscopically, and the angles defining light can be set for an intuitively and anatomically better understanding.

In this embodiment, the display means displays angles defining light stereoscopically. The angles defining light can therefore be grasped perceptively easily.

In this embodiment, the coordinate transforming means transforms the coordinates of data of slices and data of a surface. The line-of-sight angle setting means sets angles defining a line of sight or the direction of the line of sight, in which a three-dimensional image is displayed, as angles in a coordinate system having the axis of a lumen in a living body or the axis of an inserted ultrasonic probe as one of its coordinate axes. The display means displays the angles defining the line of sight in the coordinate system having the axis of a lumen in a living body or the axis of an inserted ultrasonic probe as one of its coordinate axes. Consequently, the angles defining a line of sight in which a three-dimensional image is viewed can be set for an intuitively and anatomically better understanding.

In this embodiment, the slice-surface boundary superposing means superposes a boundary line between data of slices and data of a surface as a slice-surface boundary line in a three-dimensional image. The display means displays the three-dimensional image on which the slice-surface boundary line is superposed. The data of the surface can therefore be distinguished readily from the other data.

In this embodiment, the touch panel 25 is employed. Aside from the touch panel 25, a cursor may be displayed in a screen and a pointing device such as a mouse, light pen, or trackball may be employed.

Processing relative to a threshold employed in this embodiment includes binary coding. This is attributable to the fact that the luminance value at a point which is equal to or smaller than a threshold is replaced with a O.

In this embodiment, setting the direction of a line of sight or the direction of light is performed on the displays shown in FIG. 7 or 13 using the touch panel 25. Alternatively, the displays shown in FIG. 8 or 14 may be used.

In this embodiment, slice position setting of step S2 precedes surface point extraction of step S4. The order may be inverted.

In this embodiment, when the mask switching key 21a is pressed, the display shown in FIG. 6 appears. Alternatively, the press of the mask switching key 21a may cause the display shown in FIG. 15 to appear.

In this embodiment, the ultrasonic probe 4 carries out spiral scanning. However, the present invention is not limited to the scanning employed in this embodiment but can apply to a combination of sector scanning and linear scanning, or the like.

In this embodiment, points defining a boundary are superposed at step S430. Points on adjoining scanning lines defining a boundary may be linked successively in order to form a boundary line. Furthermore, the inside of a boundary line may be painted in red or any other color different from the color of an ultrasonic tomographic image to be superposed, and the boundary line may be expressed as sides of a painted area.

In this embodiment, two-dimensional images on which points defining a boundary are superposed are listed at step S431. Alternatively, adjoining two-dimensional images may be displayed successively.

Figure 17:
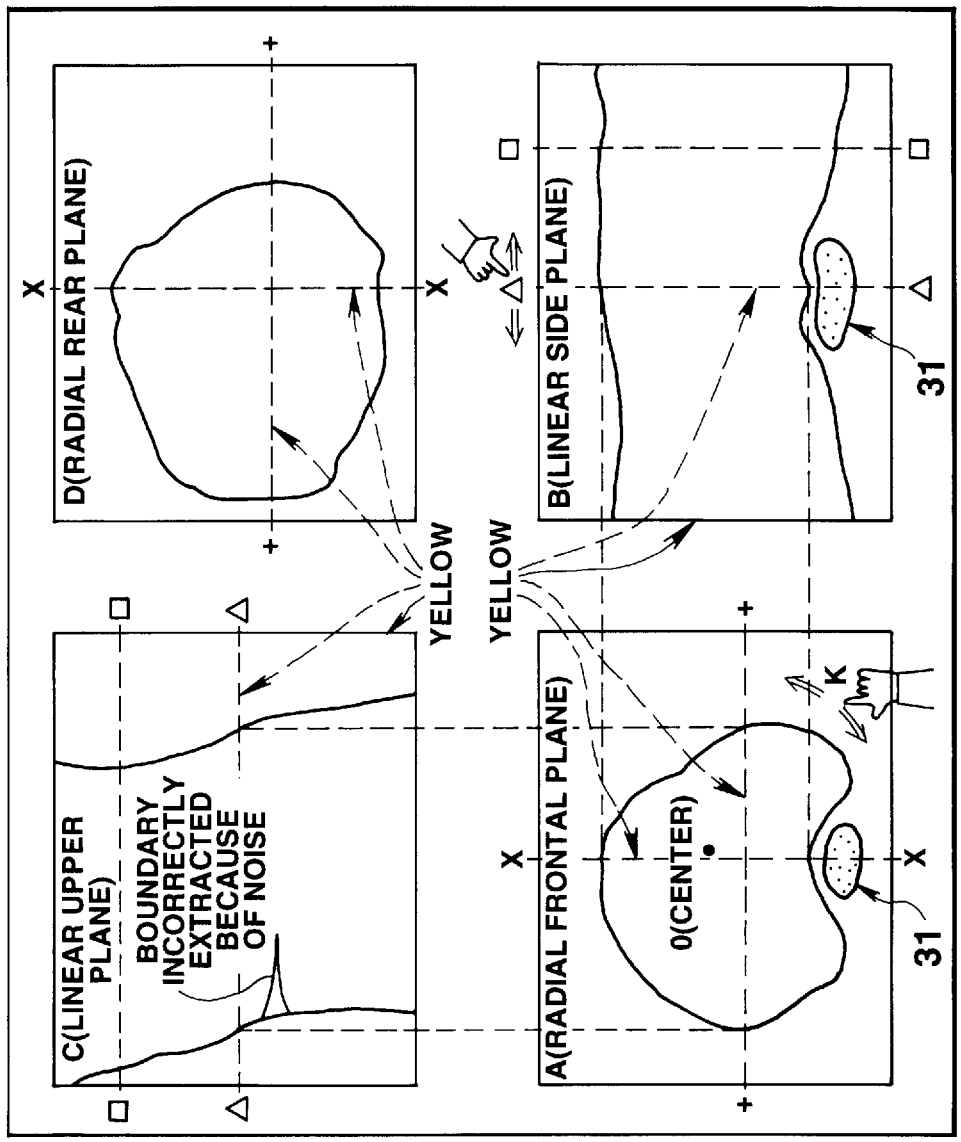
FIG. 17 is a diagram showing an exemplary example of four ultrasonic images in the second embodiment of the present invention.

Next, the second embodiment of the present invention will be described. The configuration of the second embodiment is identical to that of the first embodiment. However, the processing carried out by the CPU 13 and image processor 18 is different. Only the difference will be described. FIG. 17 shows ultrasonic images of four slices in the second embodiment.

The operations of the CPU 13 and image processor 18 will be described with reference to FIG. 17.

In this embodiment, a plurality of slices shown in FIG. 17 are displayed in the three-dimensional image processing monitor 24 instead of being listed after surface point extraction in the first embodiment (step S431 in FIG. 9). In this screen, an extracted boundary is superposed as a boundary line on the slices. In FIG. 17, a boundary extracted incorrectly because of a noise can be seen in slice C.

In this screen, similarly to the first embodiment described in conjunction with FIG. 4, other slices are modified responsively to the movement or turn of a slicing line +, ×, Δ, or □ set in a specified slice. As shown in FIG. 17, when a boundary extracted incorrectly because of a noise or the like is found, the boundary is corrected as described in conjunction with FIG. 9. The operation of this embodiment in the other aspects is identical to that of the first embodiment.

Incidentally, the CPU 13 and image processor 18 function as a tomographic image constructing means and boundary superposing means.

This embodiment has the advantages set forth below.

In this embodiment, a plurality of slices shown in FIG. 17 are displayed on the three-dimensional image processing monitor 24. An extracted boundary is superposed as a boundary line on the slices. It can therefore be judged at sight whether or not surface point extraction has been carried out properly over a plurality of consecutive two-dimensional images.

Extracted points defining the surface of an object are thus superposed as a boundary on a plurality of tomographic images showing differently-oriented slices. Part of the boundary extracted incorrectly can be discovered at sight.

Moreover, incorrectly-extracted points can be searched for by changing slices.

Next, the third embodiment of the present invention will be described.

The configuration of this embodiment is identical to that of the first embodiment. However, the processing performed by the CPU 13 and image processor 18 is different. The difference alone will be described.

The operations of the CPU 13 and image processor 18 will be described with reference to FIGS. 18 to 20.

This embodiment is different from the first embodiment in the processing of designating a start point of scanning lines shown in FIG. 9. In the other aspects, this embodiment is identical to the first embodiment. In this embodiment, the processing of steps S1811 and S1812 described in FIG. 18 is added between steps S414 and S415 in FIG. 9. The other processing is identical to the processing carried out in the first embodiment described in FIG. 9.

Figure 18:
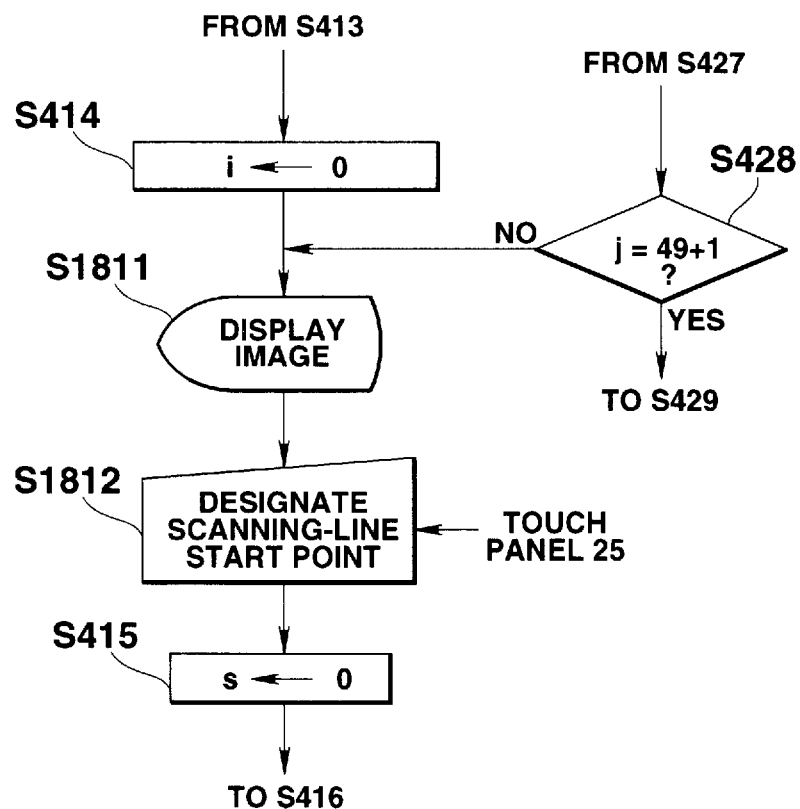
FIG. 18 is a flowchart describing part of the contents of the processing of extracting points defining a surface in the third embodiment of the present invention.

At step S1811 in FIG. 18, an image specified with variable i is displayed on the three-dimensional image processing monitor 24. Image i is shown in FIG. 19.

At step S1812 in FIG. 18, a start point of scanning lines is designated while reference is made to image i displayed on the three-dimensional image processing monitor 24. In FIG. 19, the start point of scanning lines is point O. For the designation, the position of start point O of scanning lines on the touch panel 25 is touched with a finger.

Start point O of scanning lines is thus designated. The touch panel 25 functions as a scanning-line start point designating means. In the other aspects, the third embodiment is identical to the first embodiment.

This embodiment has the advantages set forth below.

For example, when the start point of scanning lines is pre-set to point Od in FIG. 9, a boundary to be extracted includes a dead area. The dead area is shown as a hatched area in FIG. 19.

In this embodiment, at step S1812, start point O of scanning lines is designated while reference is made to the images displayed on the three-dimensional image processing monitor 24. Unlike the first embodiment, start point O of scanning lines can be designated at a position at which such a dead area is hardly created.

The other advantages are identical to those of the first embodiment.

Incidentally, the configuration of a variant of this embodiment to be described below may be adopted.

In this variant, the ultrasonic probe 4 irradiates ultrasonic waves from outside an object to be examined. The ultrasonic transducer, which is not shown, in the ultrasonic probe 4 is moved linearly while performing sector scanning. In other words, the ultrasonic probe 4 carries out in vitro sector and linear scanning that is a combination of sector scanning and linear scanning. A plurality of consecutive two-dimensional images are therefore written as three-dimensional echo data in the image data memory 17. The plurality of two-dimensional images are shown in FIG. 20. In FIG. 20, the images are numbered like image 1, image 2, etc. in the order in which they are acquired.

Figure 20:
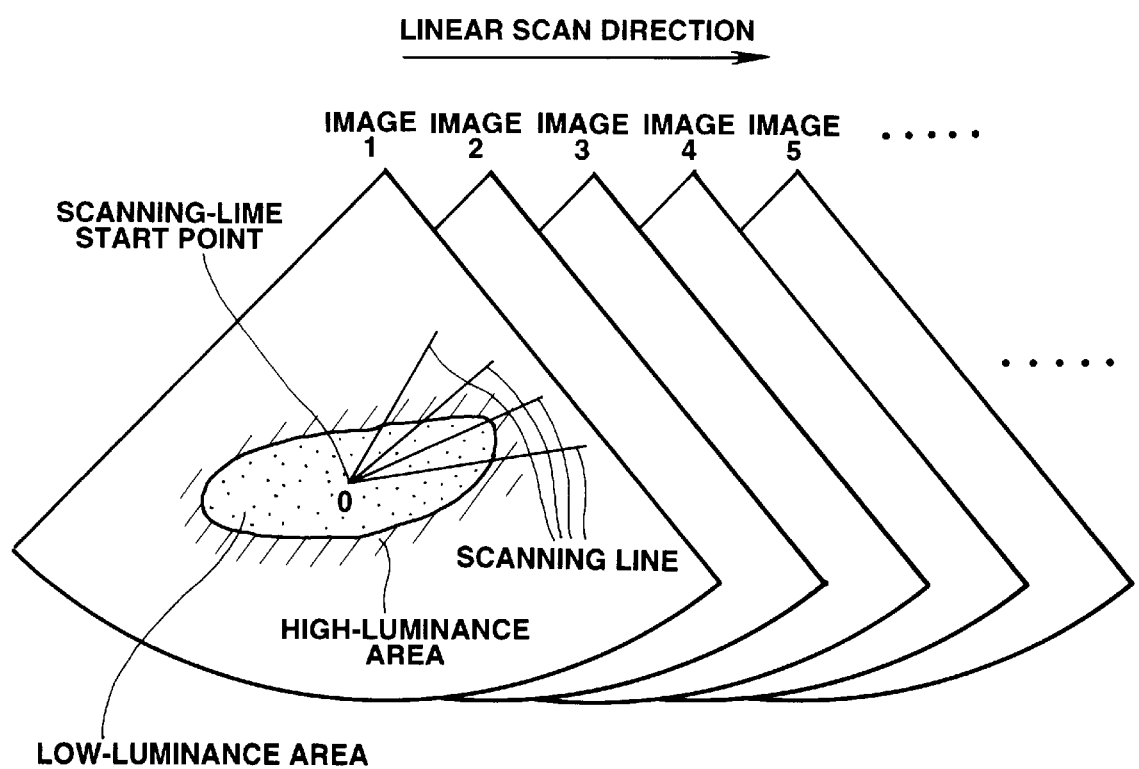
FIG. 20 is an explanatory diagram of a variant of scanning performed by an ultrasonic probe.

An area in FIG. 20 drawn with small dots indicates a low-luminance area such as a tumorous region. A surrounding hatched area indicates a high-luminance area such as the hepatic parenchyma.

In this variant, at step S1812 in FIG. 18, start point O of scanning lines is designated with reference to the images displayed on the three-dimensional image processing monitor 24. In FIG. 20, the start point is point O. For the designation, point O on the touch panel 25 is touched with a finger.

Figure 19:
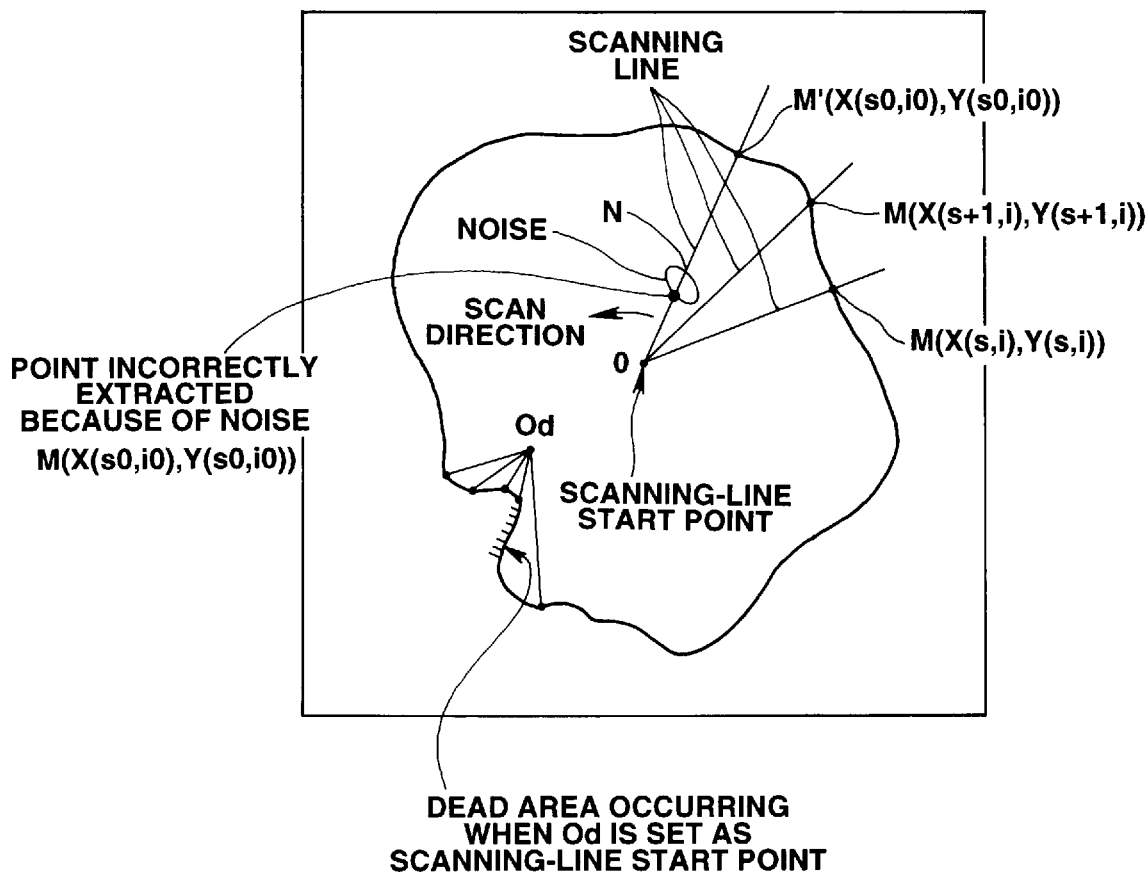
FIG. 19 is an explanatory diagram of the operation of the third embodiment.

The other components and the operation and advantages are identical to those of the third embodiment described in conjunction with FIGS. 18 and 19.

As mentioned above, when the surface extracting means or method employed in this embodiment is adopted, even if a scanning technique is changed from spiral scanning to sector and linear scanning or vice versa, a surface can be extracted accurately.

Figure 21:
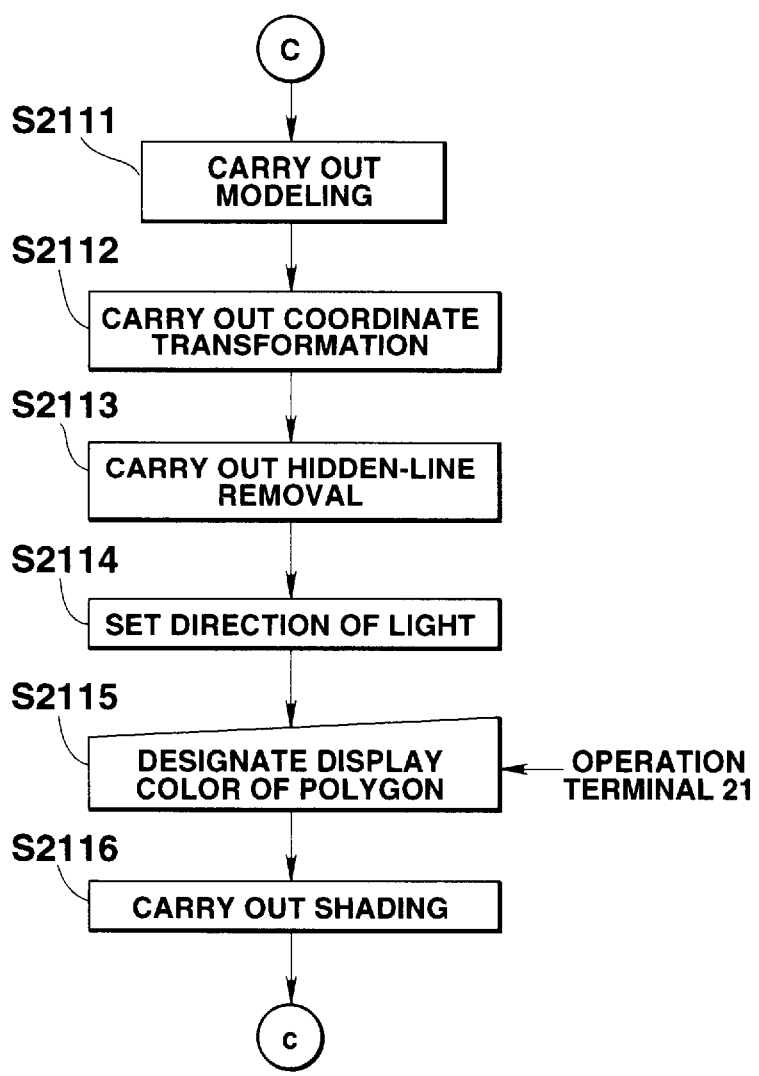
FIG. 21 is a flowchart describing the contents of the processing of shading in the fourth embodiment of the present invention.

Next, the fourth embodiment of the present invention will be described with reference to FIG. 21. FIG. 21 is a flowchart describing the contents of the processing of shading in this embodiment. The flowchart includes a step of entering a display color for a polygon at the operation terminal 21.

The configuration of the fourth embodiment is identical to that of the first embodiment. However, part of the processing performed by the CPU 13 and image processor 18 is different. The difference alone will be described.

The operations of the CPU 13 and image processor 18 will be described with reference to FIG. 21.

Steps S2111 to S2114 in FIG. 21 are identical to steps S511 to S514 in FIG. 11 relating to the first embodiment.

At step S2115 in FIG. 21, a display color for displaying a polygon is entered at the operation terminal 21.

At step S2116 in FIG. 21, the lightness of each point in each polygon is determined for a tone entered at step S2115 according to the same algorithm as that used for the processing of step S515 in FIG. 11.

With the tone entered at step S2115, a surface is shaded. Thus, shading is carried out.

As mentioned above, the operation terminal 21 functions as a display color designating means.

This embodiment has the advantages described below.

In this embodiment, at step S2115, a display color for displaying a polygon is entered in order to determine a tone for the polygon. A surface E in FIG. 16 is displayed in the display color and can be distinguished from the other part displayed in gray scale. An operator can easily judge whether each part of a three-dimensional image is the representation of image data reflecting gray-scale levels provided by echoes emanating from a living body or the representation of image data shaded using stereoscopic information such as contour.

If the real tone of the surface of an organ visible in an optical image produced by an endoscope or the like is designated as a display color, a three-dimensional image can be displayed more realistically.

The other advantages are identical to those of the first embodiment.

In this embodiment, at step S2115, a display color is entered at the operation terminal 21. An optical image such as an endoscopic image may be preserved in a storage device such as the first external storage device 19, and a typical tone of the optical image may be copied. The optical image to be preserved may be preserved for each of the esophagus, superior stomach, and duodenum. The colors of these organs may also be used as display colors.

Next, the fifth embodiment of the present invention will be described with reference to FIGS. 22 to 24.

The configuration of this embodiment is identical to that of the first embodiment. However, the processing performed by the CPU 13 and image processor 18 is different. The difference alone will be described.

The operations of the CPU 13 and image processor 18 will be described with reference to FIGS. 22 to 24.

In this embodiment, surface point extraction described in FIG. 9 is an only difference from that in the first embodiment. The other aspects of this embodiment are identical to those in the first embodiment.

Figure 22:
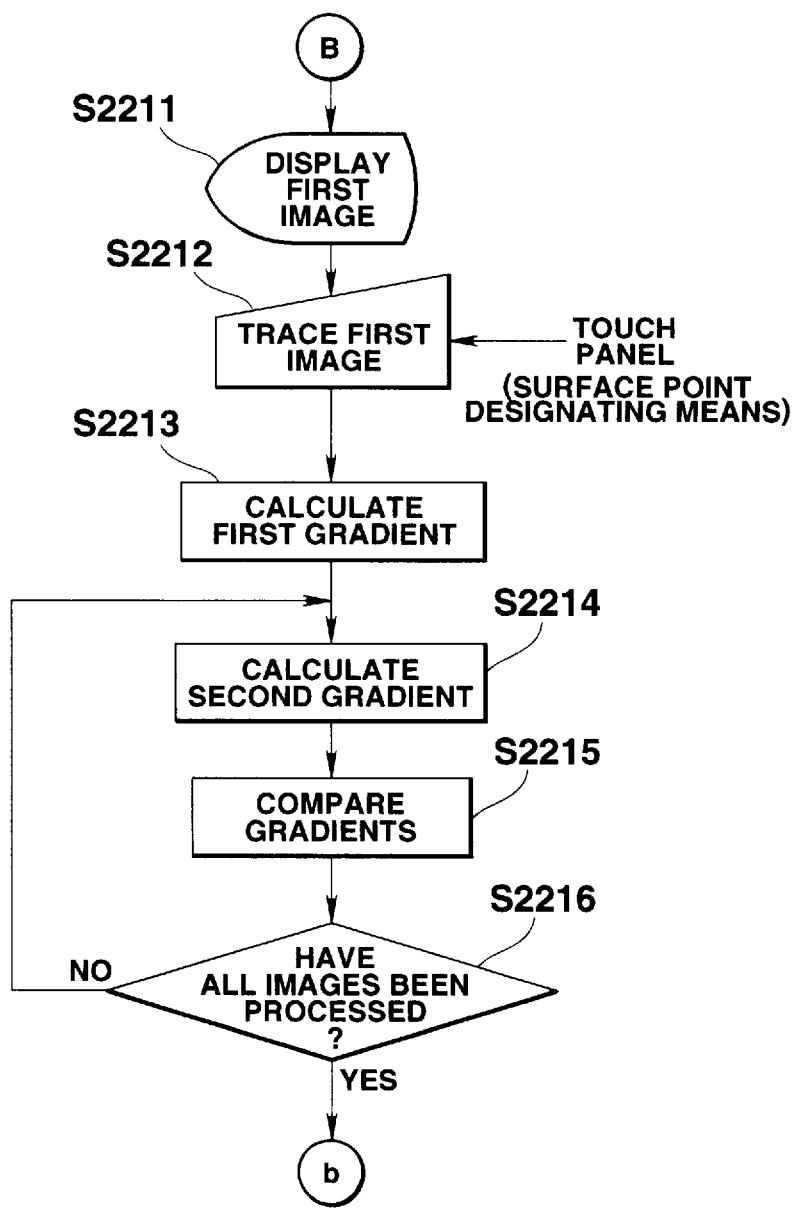
FIG. 22 is a flowchart describing the contents of the processing of surface point extraction in the fifth embodiment of the present invention.

At step S2211 in FIG. 22, the first image of 50 consecutive two-dimensional images stored in the image data memory 17 is displayed in the three-dimensional image processing monitor 24. The image is shown in FIG. 23.

At step S2212 in FIG. 22, the first image is traced. Specifically, the boundary of a two-dimensional image displayed on the three-dimensional image processing monitor 24, that is, the surface of an organ is traced manually. The tracing is carried out on the touch panel 25.

At step S2213 in FIG. 22, first gradients at traced points are calculated. Specifically, gradients (first gradients) in luminance value at points Z2, Z3, etc., and Zi, which are equiangular points on a traced trajectory starting with point Z1 defined with an equal angle $\alpha$ with certain point O in an image shown in FIG. 23 as a center, are calculated.

The first gradients are gradients in luminance along straight lines OZi (i=1, 2, 3, etc.). For calculating the gradients, a distance is made constant. FIG. 24A indicates luminance values detected along straight line OZi in the first image. The "constant distance" is denoted with $\Delta x$, and a difference in luminance value is denoted with $\Delta I$. Consequently, a gradient is expressed as follows:

$$\text{gradient} = \Delta I / \Delta x$$

At step S2214 in FIG. 22, gradients (second gradients) detected in the second image in the same directions as the directions of straight lines OZi set in the first image are calculated. A second gradient is calculated at each of points within a specified range of straight line OZi relative to point Zi' in the second image which corresponds to point Zi (See FIG. 24B). In FIG. 24B, the specified range is denoted with &x. In other words, a second gradient is calculated at each of points within the range $\delta x$ in the direction of straight line OZi and points within within the range δx in the opposite direction with point Zi' corresponding point Zi as a center.

The processing is repeated for all points within the ranges relative to all points Zi.

At step S2215 in FIG. 22, the second gradients calculated at points are compared with the first gradients calculated at points Zi. A point on straight line OZi' having a gradient closest to the first gradient is specified. FIG. 24B shows the thus specified point Zi". Thus, a boundary of the second image is specified.

Owing to the foregoing processing, even if an image contains a noise as shown in FIGS. 23 and 24A, the noise can be eliminated to some extent by utilizing the range δx. If a noise should lie within the range δx, it is quite rare that a gradient at any point becomes close to the first gradient. In any case, therefore, points having gradients closest to the first gradients can be specified as points defining a boundary in the second image.

At step S2216 in FIG. 22, control is branched depending on whether or not processing all two-dimensional images is completed. If the processing is not completed, control is jumped to step S2214. If the processing is completed, surface point extraction is terminated. After control is jumped to step S2214, the gradients detected in the second image are regarded as the first gradients, and the gradients detected in the third image are regarded as the second gradients. The foregoing processing is then repeated. The same applies to the subsequent images.

Thus, points defining a surface are extracted.

As mentioned previously, the CPU 13 and image processor 18 function as a first gradient calculating means, second gradient calculating means, and surface point specifying means.

The touch panel 25 functions as a surface point designating means.

This embodiment has the advantages described below.

In this embodiment, at step S2214, a second gradient is calculated at points within a specified range relative to a point at which a first gradient is calculated. At step S2215, the second gradients are compared with the first gradients in order to extract points defining a surface. A point included in a noise outside the range will therefore not be extracted incorrectly as one of points defining a surface. The noise is shown in FIGS. 23 and 24.

The other advantages are identical to those of the first embodiment.

Next, the sixth embodiment of the present invention will be described with reference to FIGS. 25 to 30.

The configuration of this embodiment is identical to that of the first embodiment. However, the processing performed by the CPU 13 and image processor 18 is different. Surface point extraction of step S4 in FIG. 2 concerning the first embodiment is different from that in this embodiment. The processing will be described.

Image processing performed by the CPU 13 and image processor 18 will be described with reference to FIGS. 25 to 30.

Figure 25:
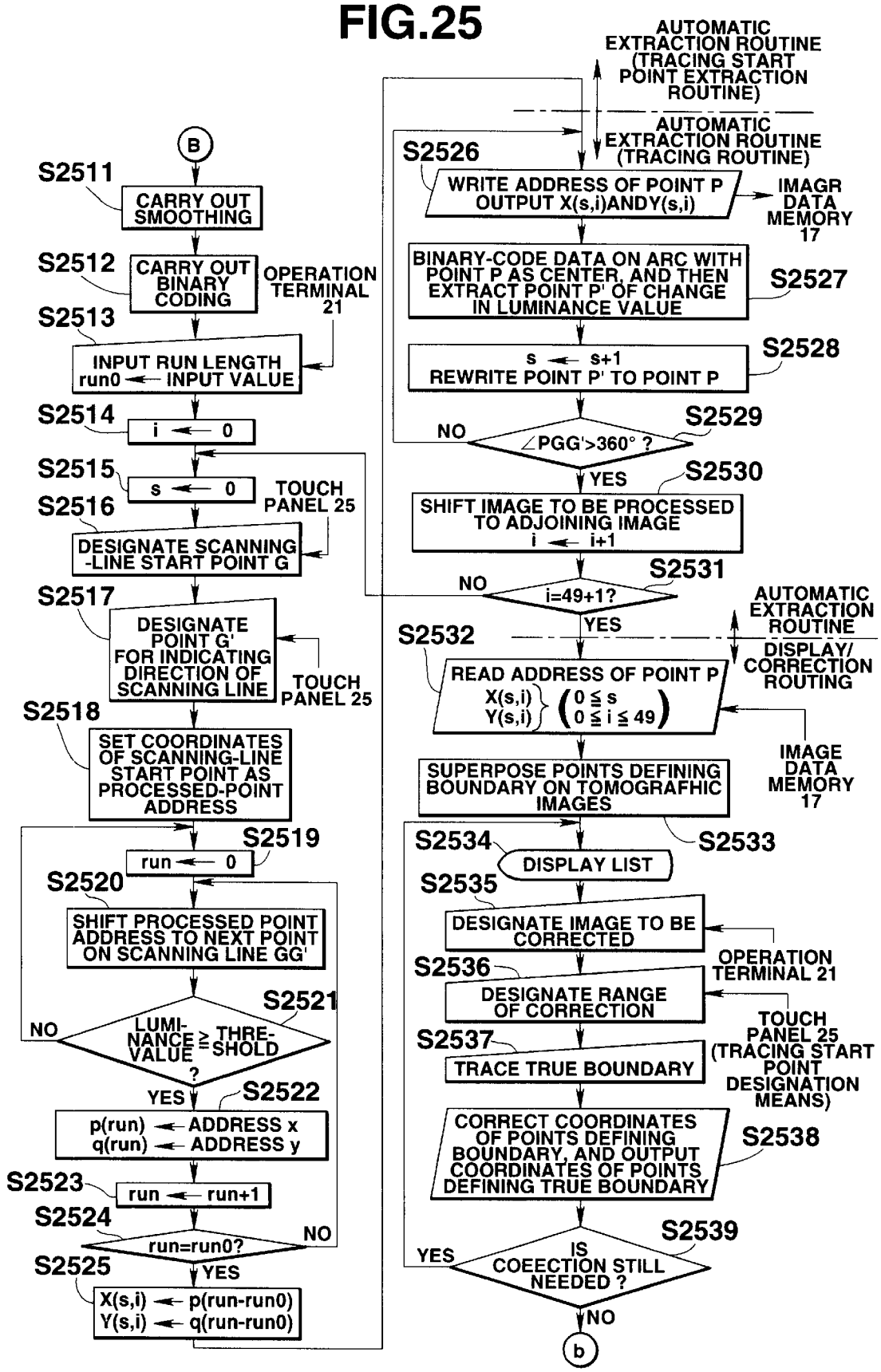
FIG. 25 is a flowchart describing the contents of the processing of surface point extraction in the sixth embodiment of the present invention.

Steps S2511 to S2531 in FIG. 25 constitute an automatic extraction routine for automatically extracting points defining a surface, and steps S2532 to S2539 constitute a display/correction routine for displaying and correcting an automatically-extracted boundary.

Furthermore, within the automatic extraction routine, steps S2511 to S2525 constitute a tracing start point extraction routine for extracting a tracing start point, and steps S2526 to S2531 constitute a tracing routine for automatically extracting points defining a surface through tracing.

The tracing start point extraction routine within the automatic extraction routine will be described below.

At step S2511 in FIG. 25, image data is smoothed. The unit of smoothing can be varied to be optimal in terms of ultrasonic resolution attainable during scanning made by the ultrasonic probe 4.

At step S2512 in FIG. 25, image data is binary-coded. The luminance values at points which are equal to or smaller than a certain threshold are replaced with 0s, while the luminance values at points which are larger than the threshold are replaced with 1s.

At step S2513 in FIG. 25, a length used to recognize a run of points, at which data values are larger than the threshold, having a length larger than the length as a noise is assigned to variable run0. The entry of the length is carried out at the operation terminal 21.

At step S2514 in FIG. 25, O is assigned to variable 1. Variable i indicates the number of a two-dimensional image to be processed at present among a plurality of consecutive two-dimensional images written as image data in the image data memory 17. In this embodiment, assuming that 50 two-dimensional images shall be processed, the following relationship is established:

$$0 \leq i \leq 49$$

At step S2515 in FIG. 25, O is assigned to variable S. Variable s is a variable used to number points, which define a boundary, extracted by performing tracing that will be described later.

Figure 26:
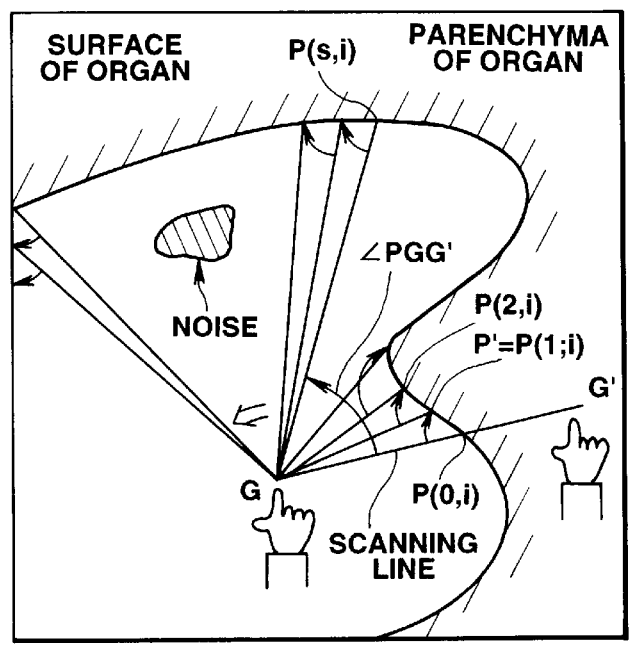
FIG. 26 is an explanatory diagram showing a scene of continuously tracing points defining a boundary from a start point P using a two-dimensional image i.

At step S2516 in FIG. 25, one point G in a screen is designated. Point G shall be termed a start point of scanning lines and is shown in FIG. 26. Specifically, a user touches a point in a screen on the touch panel 25 with his/her finger so as to designate point G.

At step S2517 in FIG. 25, another point G' in the screen is designated. Specifically, the user touches a point in the screen on the touch panel 25. At this time, segment GG' appears, as shown in FIG. 26, in a two-dimensional image displayed on the three-dimensional image processing monitor 24 responsively to the movement of the user's finger. Segment GG' shall be termed a scanning line.

At step S2518 in FIG. 25, the coordinates of point G are set as a processed-point address. The processed-point address consists of address x and address y that correspond the x and y coordinates of a currently-processed point.

At step S2519 in FIG. 25, O is assigned to variable run. Variable run is used to measure the length of a run.

At step S2520 in FIG. 25, the processed-point address is shifted to the next point on scanning line GG'.

At step S2521 in FIG. 25, it is judged whether the luminance value at the point indicated with the processed-point address is larger or smaller than the threshold used for binary coding performed at step S2512. If the luminance value is larger, control is jumped to step S2522. If the luminance value is smaller, control is jumped to step S2519.

At step S2522 in FIG. 25, address x of the processed-point address is assigned to the run-th variable p(run) of one-dimensional array variables p, and address y thereof is assigned to the run-th variable q(run) of one-dimensional array variables q.

At step S2523 in FIG. 25, 1 is added to variable run.

At step S2524 in FIG. 25, it is judged whether or not variable run agrees with run0. If the values agree with each other, control is passed to step S2525. If the values disagree with each other, control is jumped to step S2520.

At step S2525 in FIG. 25, q(run-run0) is assigned to two-dimensional array variable X(s, i), and q(run-run0) is assigned to two-dimensional array variable Y(s, i). A point closest to the start point of scanning lines is extracted as coordinates (X(s, i), Y(s, i)) from a run of consecutive points on the scanning line, at which luminance values are larger than the threshold, having a length larger than length runO or larger.

Next, the tracing routine within the automatic extraction routine will be described.

At step S2526 in FIG. 25, coordinates X(s, i) and Y(s, i) are output to the image data memory 17. In other words, at step S2526, the address of point P shown in FIG. 26 is written in the image data memory 17.

Figure 27:
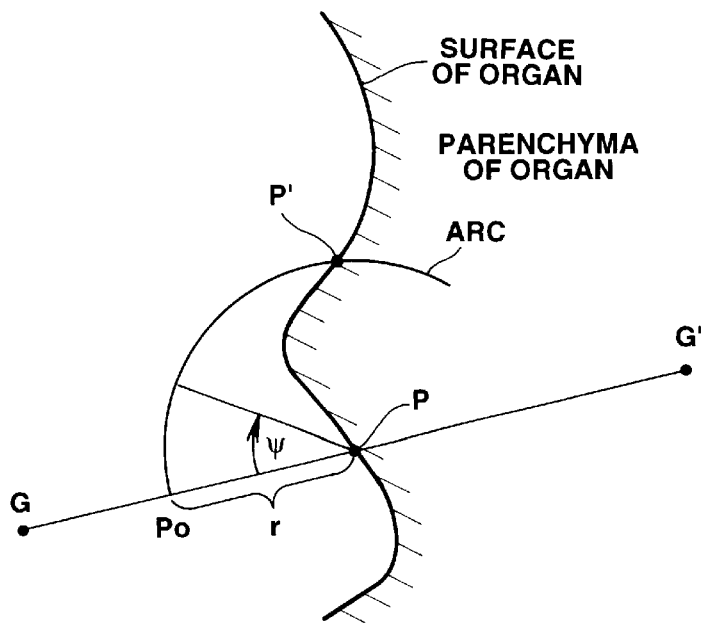
FIG. 27 is an explanatory diagram showing part of FIG. 26 in an enlarged form.

At step S2527 in FIG. 25, new point P' defining a boundary is extracted by retrieving a data value from points starting with an intersection Po between segment GP and an arc, which has a radius r and has point P as a center as shown in FIG. 27 showing part of FIG. 26 in enlargement, along the arc. This retrieval is carried out as described below.

To begin with, in FIG. 26, the outside of the surface of an organ is the parenchyma thereof, and the inside, that is, part including point G is usually an ultrasonic medium such as water. Binary-coded luminance values detected on the arc in FIG. 27 are indicated as shown in FIG. 28.

Figure 28:
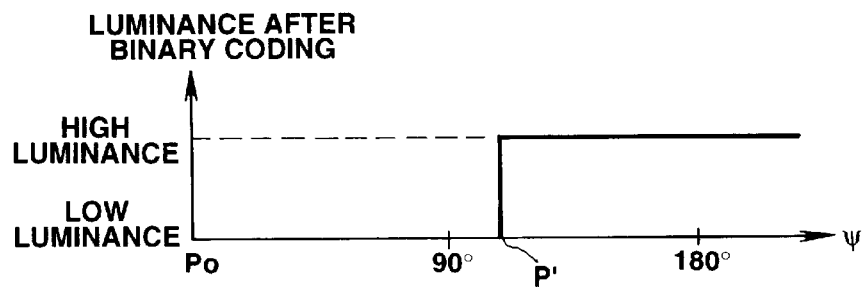
FIG. 28 is an explanatory diagram of the operation of binary coding performed at step S2527 in FIG. 25.

In FIG. 28, the axis of abscissae indicates the angle ψ with respect to segment GP. Point Po is set in the ultrasonic medium and has a low luminance. A point at which the low luminance changes to a high luminance with the variation of the angle ψ corresponds to point P' defining a boundary shown in FIGS. 26 and 27. Thus, point P' is extracted by retrieving a luminance value from points starting with point Po in FIG. 28 and thus searching for a point at which the luminance value undergoes a change first.

At step S2528 in FIG. 25, 1 is added to variable s. Point P' then is rewritten to point P.

At step S2529 in FIG. 25, angle ∠ PGG' with respect to rewritten point P is calculated, and it is judged whether the angle ∠PGG' is larger or smaller than 3600. If the angle is larger, control is passed to step S2530. If the angle is smaller, control is jumped to step S2526. At step S2528, point P' is rewritten to point P. The angle ∠PGG' is therefore actually comparable to angle ∠P'GG' shown in FIG. 27.

At step S2530 in FIG. 25, 1 is added to variable i. That is to say, the two-dimensional image to be processed is shifted to an adjoining two-dimensional image.

At step S2531 in FIG. 25, it is judged whether or not variable i agrees with 49+1. In other words, it is judged whether or not processing the last two-dimensional image among all the two-dimensional images written in the image data memory 17 is completed. If the values agree with each other, control is passed to step S2532. If the values disagree with each other, control is jumped to step S2515.

Thus, within the automatic extraction routine consisting of the tracing start point extraction routine and tracing routine, coordinates (X(s, i), Y(s, i)) of points (s, i) recognized to define the surface of a body cavity, that is, a boundary are obtained for all two-dimensional images stored in the image data memory 17, and then written successively in the image data memory 17.

Figure 29:
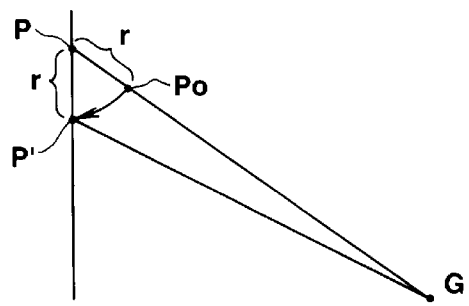
FIG. 29 is an explanatory diagram of the processing of treating an edge of an image.

Incidentally, the parenchyma of an organ dies out in the left-hand part of the screen in FIG. 26. In this state, searching for point P(s, i) is suspended. At step S2527, therefore, as shown in FIG. 29, while a point at which the luminance value detected at point Po first undergoes a change is being searched for, if an arc dies out at an edge of an image, an intersection between the arc and the edge of the image is extracted as point P'.

Next, the display/correction routine will be described.

At step S2532 in FIG. 25, coordinates X(s, i) and Y(s, i) of all points defining a boundary which are extracted from all images written in the image data memory 17 are read.

In short, coordinates of points P recognized to define a boundary are read from the image data memory 17.

At step S2533 in FIG. 25, points defining a boundary of which coordinates are indicated with X(s, i) and Y(s, i) are superposed on each two-dimensional image represented in gray scale.

At step S2534 in FIG. 25, two-dimensional images on which points defining a boundary are superposed and which are represented in gray scale are listed on the three-dimensional image processing monitor 24.

Figure 30:
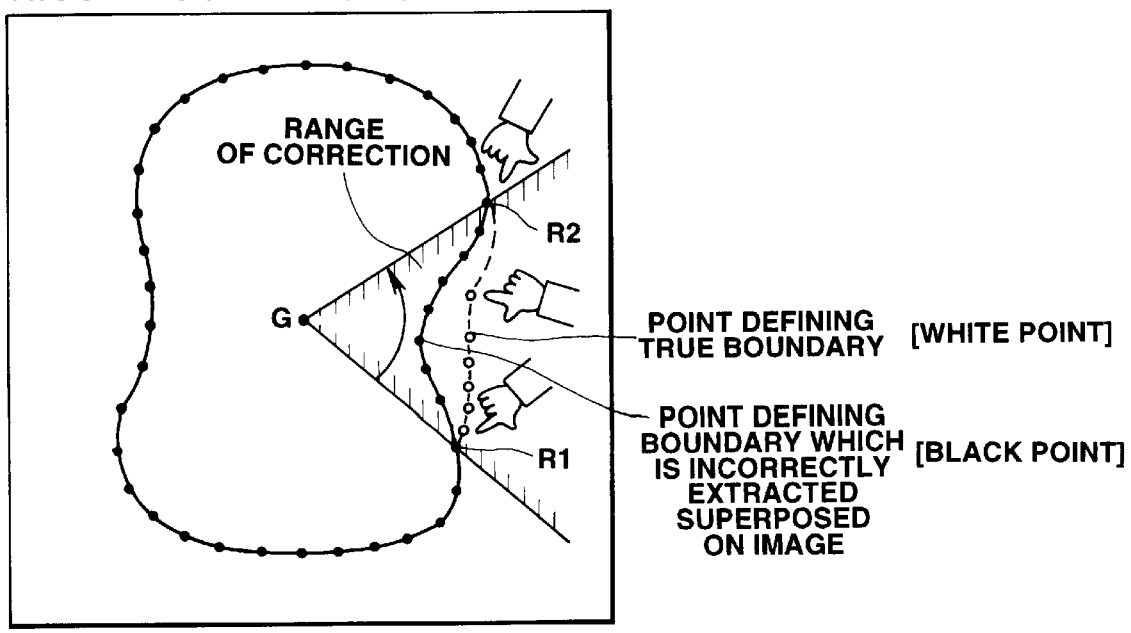
FIG. 30 is an explanatory diagram showing a scene of correcting incorrectly-extracted part of a boundary.

At step S2535 in FIG. 25, two-dimensional image iO having part of a boundary thereof extracted incorrectly is selected from among the listed two-dimensional images, and designated. Two-dimensional image iO is shown in FIG. 30.

At step S2536 in FIG. 25, the user designates a range of correction in two-dimensional image iO on the touch panel 25. Specifically, as shown in FIG. 30, the range of correction is designated by specifying limits R1 and R2 on an incorrectly-extracted boundary, and determining angle ∠R1GR2. The range of correction is indicated as a hatched area in FIG. 30.

At step S2537 in FIG. 25, the user traces a true boundary manually on the touch panel 25. The tracing is shown in FIG. 30. That is to say, points defining a true boundary which are indicated with white dots are traced instead of points incorrectly extracted as points defining a boundary and indicated with black dots.

At this time, points P(s, i) defining a true boundary are set equidistantly along a trajectory traced by the user within the range defined with angle ∠R1GR2.

At step S2538 in FIG. 25, the coordinates of the points incorrectly extracted as points defining a boundary are deleted from the image data memory 17, and the coordinates of the points P(s, i) defining a true boundary which are set at step S2537 are output as two-dimensional array variables X(s, i) and Y(s, i) to the image data memory 17. At this time, the two-dimensional array variables X(s, i) and Y(s, i) in the image data memory 17 are re-sorted to be numbered according to points P(s, i) (s=0, 1, etc.) as shown in FIG. 26.

At step S2539 in FIG. 25, a message asking if correction is still needed is displayed on the three-dimensional image processing monitor 24. The user makes a response at the operation terminal 21. If correction is still needed, control is jumped to step S2534. If correction is not needed any longer, surface point extraction is terminated.

As mentioned above, the display/correction routine corrects points incorrectly extracted because of a residue in a body cavity or a noise.

As described previously, the CPU 13 and image processor 18 function as a surface tracing means and luminance change point retrieving means.

The touch panel 25 functions as a tracing start point designating means.

This embodiment has the advantages described below.

In this embodiment, points defining the surface of a desired object are automatically traced in a plurality of consecutive ultrasonic tomographic images. For example, a point included in the noise shown in FIG. 26 will not be extracted as a point defining the surface of an organ. That is to say, the surface of a desired object can be extracted and expressed accurately without interference by a noise or the like.

In this embodiment, an image is smoothed at step S2511. Before points defining a surface are extracted along each scanning line, a noise can be eliminated to some extent.

In this embodiment, points defining a boundary are superposed on ultrasonic tomographic images at step S2533, and the ultrasonic tomographic images are listed at step S2534. The images to be superposed and displayed may be images processed relative to a threshold or binary-coded images. However, if ultrasonic raw images represented in gray scale are listed as they are in this embodiment, since points defining a boundary are usually superposed on ultrasonic images used for diagnosis, which image should be corrected can be determined more distinctively.

In this embodiment, correction can be achieved while reference is made to the image shown in FIG. 30. A boundary can therefore be corrected properly.

In this embodiment, at step S2513, a length used to recognize a run, of which length is equal to or smaller than the length, as a noise is entered at step S2513. For designating a tracing start point, noises of various sizes can be eliminated.

The other advantages are identical to those of the first embodiment.

In this embodiment, the touch panel 25 is employed. Aside from the touch panel 25, a cursor may be displayed in a screen, and a pointing device such as a mouse, light pen, or trackball may be employed.

In this embodiment, binary coding is carried out at step S2512. Another processing relative to a threshold may be adopted.

In this embodiment, points defining a boundary are superposed at step S2533. Points P(s, i) defining a boundary may be linked in ascending order of numbers s. Furthermore, the inside of a boundary may be painted in red or any other color different from the color of an ultrasonic tomographic image to be superposed, and the boundary may be expressed as sides of the painted area.

In this embodiment, two-dimensional images on which points defining a boundary are superposed are listed at step S2534. Alternatively, adjoining two-dimensional images may be displayed successively.

In this embodiment, the present invention is presumably adapted to a luminal organ such as the stomach. Alternatively, the present invention can be adapted to a non-luminal organ such as the liver or pancreas.

Next, the seventh embodiment of the present invention will be described with reference to FIGS. 31 and 32.

The configuration of this embodiment is identical to that of the sixth embodiment. However, the processing performed by the CPU 13 and image processor 18 is different. The difference alone will be described.

The operations of the CPU 13 and image processor 18 will be described with reference to FIGS. 31 and 32.

In this embodiment, the processing of designating a start point of scanning lines described in FIG. 25 is different from that in the sixth embodiment. In the other aspects, this embodiment is identical to the sixth embodiment. In this embodiment, as shown in FIG. 31, the processing of steps S3111, S3112, and S3113 is added. The other steps described in FIG. 31 are identical to those of corresponding numbers shown in FIG. 25 concerning the sixth embodiment.

Figure 31:
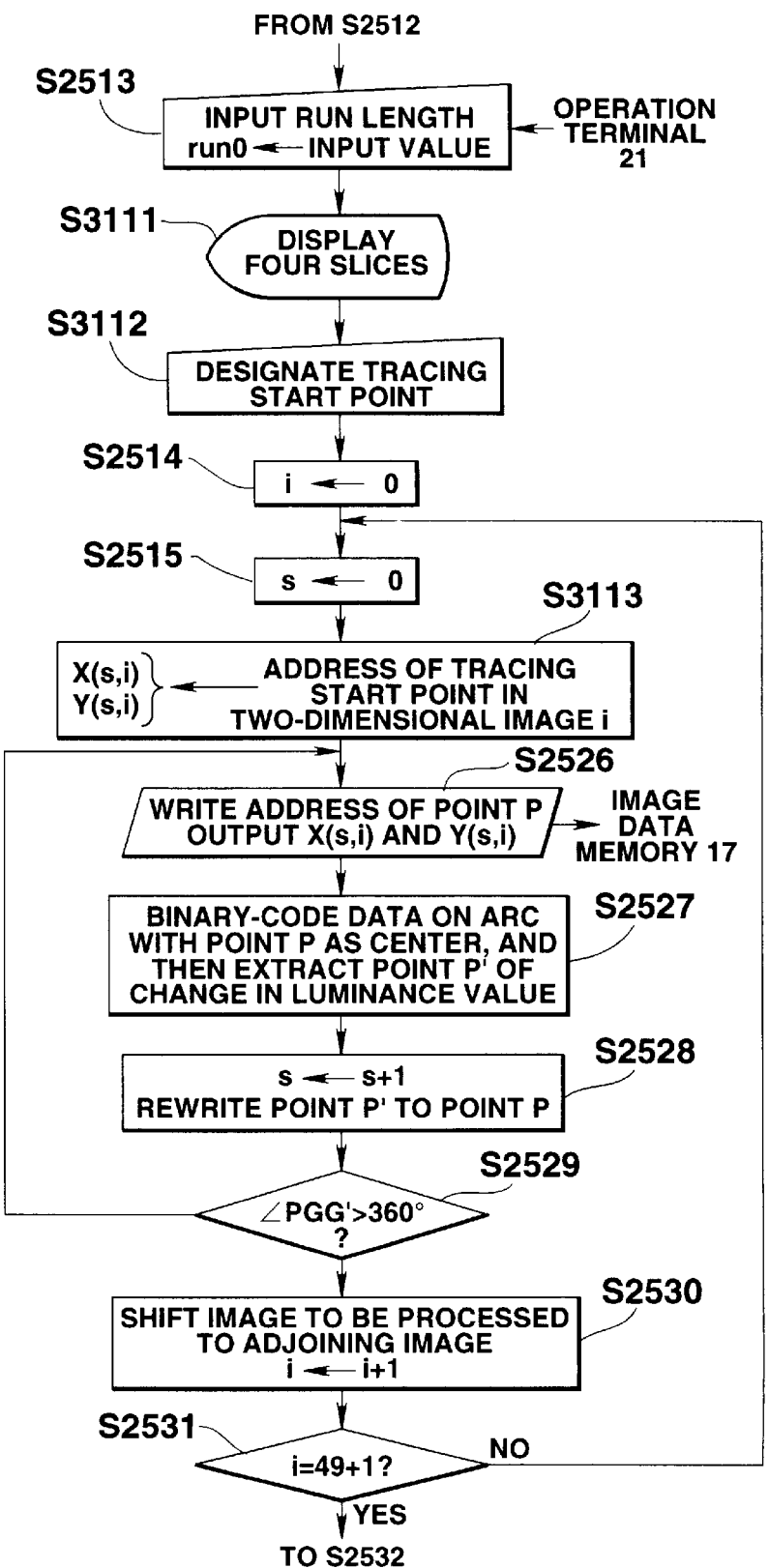
FIG. 31 is a flowchart describing part of the contents of the processing of surface point extraction in the seventh embodiment of the present invention.
Figure 32:
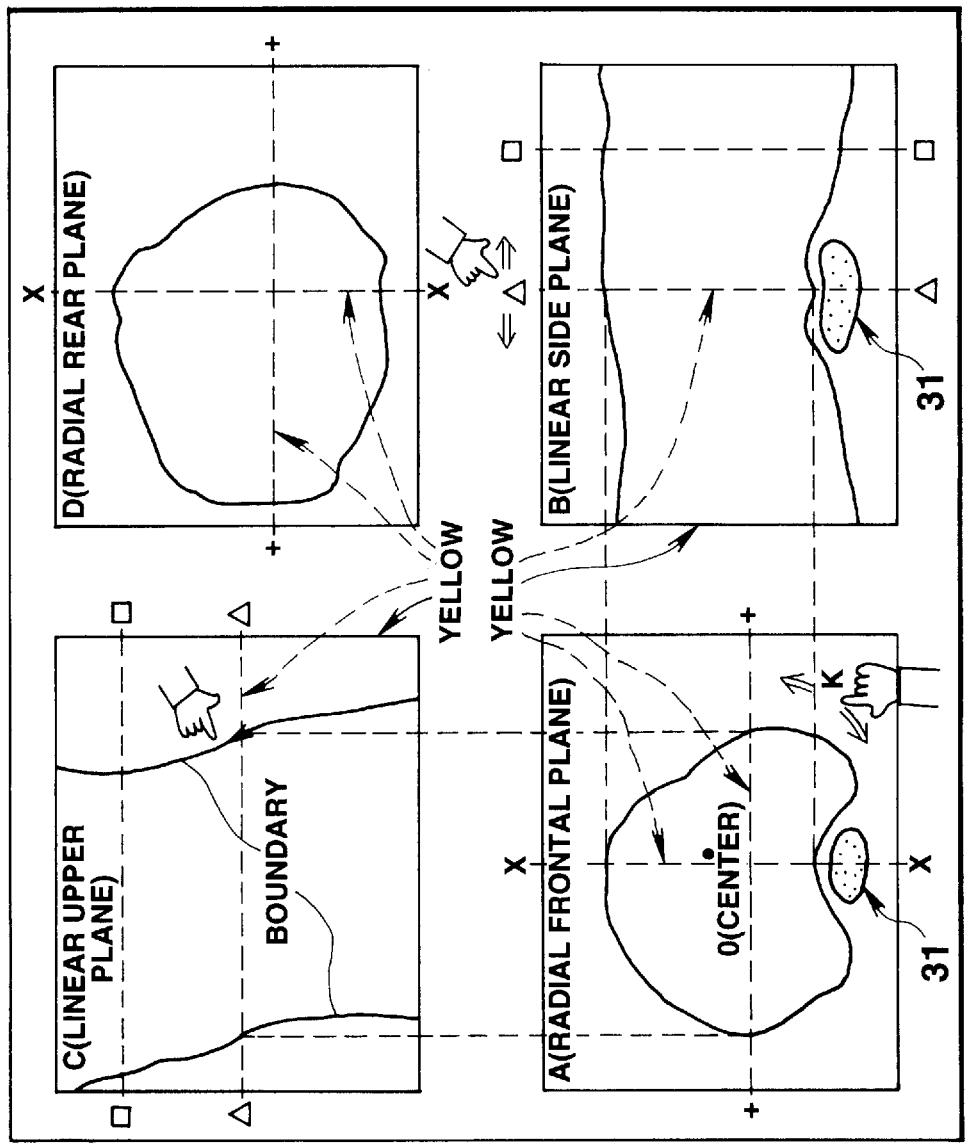
FIG. 32 is an explanatory diagram of the operation of designating the start point of scanning lines.

At step S2513 and subsequent step S3111 in FIG. 31, four slice images shown in FIG. 32 are displayed on the three-dimensional image processing monitor 24. The positional relationship among the four slices is identical to that in FIG. 4.

At step S3112 in FIG. 31, a tracing start point is designated on a linear plane of slice B or C while reference is made to the images appearing on the three-dimensional image processing monitor 24. For the designation, a bold line in FIG. 32 on the touch panel 25 is traced with a finger. Since the linear plane is constructed using 50 consecutive two-dimensional images, a tracing start point can be designated for the 50 two-dimensional images merely by tracing a boundary expressed on the linear plane.

Thus, a tracing start point is designated.

Since a tracing start point can be designated simultaneously for a plurality of images, the processing from step S2516 to step S2525 in FIG. 25 is omitted. At step S3113 in FIG. 31, the address of the tracing start point for two-dimensional images i is assigned to two-dimensional array variables X(s, i) and Y(s, i).

As described previously, the touch panel 25 functions as a tracing start point designating means.

This embodiment has the advantages described below.

In this embodiment, at step S3112, a tracing start point is designated simultaneously for 50 images while reference is made to images appearing on the three-dimensional image processing monitor 24. Handling is therefore easier than that in the six embodiment in which a tracing start point must be designated repeatedly for each of 50 images.

The other advantages are identical to those of the sixth embodiment.

Incidentally, an embodiment formed by combining parts of the aforesaid embodiments also belong to the present invention.

What is claimed is:

1. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a surface point extracting means for extracting points defining the surface of a desired object from the three-dimensional echo data stored in said three-dimensional echo data memory means;

a shading means for shading data of a surface defined with the points extracted by said surface point extracting means;

a synthesizing means for synthesizing data of the slices whose positions are set by said slice position setting means and data of the surface shaded by said shading means so as to construct a three-dimensional image; and a display means for displaying the three-dimensional image constructed by said synthesizing means, wherein said surface point extracting means scans the three-dimensional echo data along each scanning line from a start point of scanning lines to a far point, and extracts a point closest to the start point of scanning lines from each run of consecutive points, at which luminance values exceed a certain threshold, having a length larger than a set length.

2. A diagnostic ultrasonic imaging system according to claim 1, wherein said run extracting means can vary the value of the set length.

3. A diagnostic ultrasonic imaging system, comprising:

an ultrasonic probe for transmitting ultrasonic waves to a living body, receiving echoes from the living body, and producing a plurality of ultrasonic tomographic images depicting a three-dimensional area;

a three-dimensional echo data memory means for storing data that is provided by echoes emanating from the three-dimensional area and represents the plurality of consecutive ultrasonic tomographic images produced by said ultrasonic probe;

a slice position setting means for setting the positions of desired slices using the three-dimensional echo data stored in said three-dimensional echo data memory means;

a surface point extracting means for extracting points defining the surface of a desired object from the three-dimensional echo data stored in said three-dimensional echo data memory means;

a shading means for shading data of a surface defined with the points extracted by said surface points extracting means;

a synthesizing means for synthesizing data of the slices whose positions are set by said slice position setting means and data of the surface shaded by said shading means so as to construct a three-dimensional image; and a display means for displaying the three-dimensional image constructed by said synthesizing means, wherein said surface point extracting means includes a boundary superposing means for superposing the extracted points defining the surface of an object on all of a plurality of consecutive ultrasonic tomographic images, or on a specified ultrasonic tomographic image.

4. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a surface point extracting means for extracting points defining the surface of a desired object from the three-dimensional echo data stored in said three-dimensional echo data memory means;

a shading means for shading data of a surface defined with the points extracted by said surface point extracting means;

a synthesizing means for synthesizing data of the slices whose positions are set by said slice position setting means and data of the surface shaded by said shading means so as to construct a three-dimensional image; and a display means for displaying the three-dimensional constructed by said synthesizing means, wherein said surface point extracting means includes: a tomographic image constructing means for constructing a plurality of tomographic images depicting differently-oriented slices using image data of the three-dimensional echo data; and a boundary superposing means for superposing the extracted points defining the surface of an object on the tomographic images constructed by said tomographic image constructing means.

5. A diagnostic ultrasonic imaging system according to claim 3 or 4, wherein said surface point extracting means includes a boundary correcting means for correcting a boundary superposed by said boundary superposing means, and corrects points defining the surface of an object to be extracted according to the boundary corrected by said boundary correcting means.

6. A diagnostic ultrasonic imaging system according to claim 5, wherein said surface point extracting means includes a run extracting means that scans the three-dimensional echo data along each scanning line from a start point of scanning lines to a far point, and extracts a point closest to the start point of scanning lines from each run of consecutive points, at which luminance values exceed a certain threshold, having a length larger than a given length;

said boundary correcting means includes a corrected scanning line designating means for use in designating a scanning line containing a point to be corrected; and a point on the scanning line designated with said corrected scanning line designating means, which is closest to the start point of scanning lines secondly to a point extracted by said run extracting means, is extracted.

7. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a synthesizing means for constructing a three-dimensional image using data of the slices whose positions are set by said slice position setting means; and a display means for displaying the three-dimensional image constructed by said synthesizing means, wherein said slice position setting means includes: a tomographic image constructing means for constructing a plurality of tomographic images depicting differently-oriented slices using image data of the three-dimensional echo data;

a slicing line moving means for moving slicing lines indicating the positions of slices in a plurality of tomographic images constructed by said tomographic image constructing means; and a tomographic image turning means for turning a specified tomographic image among the plurality of tomographic images constructed by said tomographic image constructing means, and the plurality of tomographic images constructed by said tomographic image constructing means except the specified tomographic image are modified responsively to the turn of the specified tomographic image made by said tomographic image turning means.

8. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a synthesizing means for constructing a three-dimensional image using data of the slices whose positions are set by said slice position setting means; and a display means for displaying the three-dimensional image constructed by said synthesizing means, wherein said slice position setting means includes: a tomographic image constructing means for constructing a plurality of tomographic images depicting differently-oriented slices using image data of the three-dimensional echo data; and a slicing line moving means for moving slicing lines indicating the positions of slices in the plurality of tomographic images constructed by said tomographic image constructing means, and said tomographic image constructing means includes a masking means for displaying data used by said synthesizing means for constructing the three-dimensional image and the other data in different forms.

9. A diagnostic ultrasonic imaging system according to claim 8, wherein said masking means includes a display form designating means for use in designating whether or not data used by said synthesizing means for constructing the three-dimensional image and the other data are displayed in different forms.

10. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a surface point extracting means for extracting points defining the surface of a desired object from the three-dimensional echo data stored in said three-dimensional echo data memory means;

a shading means for shading data of a surface defined with the points extracted by said surface point extracting means;

a synthesizing means for synthesizing data of the slices whose positions are set by said slice position setting means and data of the surface shaded by said shading means so as to construct a three-dimensional image; and a display means for displaying the three-dimensional image constructed by said synthesizing means, wherein said shading means includes a light angle setting means for setting angles defining light used for shading as angles in a coordinate system having the axis of a lumen in a living body or the axis of an inserted ultrasonic probe as one of its coordinate axes, and said display means displays the angles defining light in the coordinate system having the axis of a lumen in a living body or the axis of an inserted ultrasonic probe as one of its coordinate axes.

11. A diagnostic ultrasonic imaging system according to claim 10, wherein said display means displays the angles defining light stereoscopically.

12. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a surface point extracting means for extracting points defining the surface of a desired object from the three-dimensional echo data stored in said three-dimensional echo data memory means;

a shading means for shading data of a surface defined with the points extracted by said surface point extracting means;

a synthesizing means for synthesizing data of the slices whose positions are set by said slice position setting means and data of the surface shaded by said shading means so as to construct a three-dimensional image; and a display means for displaying the three-dimensional image constructed by said synthesizing means, said diagnostic ultrasonic imaging system further comprising:

a coordinate transforming means for transforming the coordinates of data of the slices whose positions are set by said slice position setting means and of data of the surface defined with the points extracted by said surface point extracting means, wherein said coordinate transforming means includes a line-of-sight angle setting means for setting angles defining a line of sight or the direction of a line of sight, in which the three-dimensional image is displayed, as angles in a coordinate system having the axis of a lumen in a living body or the axis of an inserted ultrasonic probe as one of its coordinate axes, said display means displays the angles defining a line of sight in the coordinate system having the axis of a lumen in a living body or the axis of an inserted ultrasonic probe as one of its coordinate axes.

13. A diagnostic ultrasonic imaging system, comprising:

a three-dimensional echo data memory means for transmitting ultrasonic waves to a living body, receiving echoes from the living body, and storing data provided by the echoes emanating from a three-dimensional area;

a slice position setting means for setting the positions of desired slices using the three-dimensional echo data stored in said three-dimensional echo data memory means;

a surface point extracting means for extracting points defining the surface of a desired object from the three-dimensional echo data stored in said three-dimensional echo data memory means;

a shading means for shading data of a surface defined with the points extracted by said surface point extracting means;

a synthesizing means for synthesizing data of the slices whose positions are set by said slice position setting means and data of the surface shaded by said shading means so as to construct a three-dimensional image; and a display means for displaying the three-dimensional image constructed by said synthesizing means, wherein said synthesizing means includes a slice-surface boundary superposing means for superposing a boundary line between data of the slices and data of the surface as a slice-surface boundary line on the three-dimensional image, and said display means displays the three-dimensional image on which the slice-surface boundary line is superposed by said slice-surface boundary superposing means.

14. A diagnostic ultrasonic imaging system according to claim 1, further comprising a scanning-line start point designating means for use in designating the position of a start line of scanning lines.

15. A diagnostic ultrasonic imaging system, comprising:
   a three-dimensional echo data memory means for transmitting ultrasonic waves to a living body, receiving echoes from the living body, and storing data provided by the echoes emanating from a three-dimensional area;
   a slice position setting means for setting the positions of desired slices using the three-dimensional echo data stored in said three-dimensional echo data memory means;
   a surface point extracting means for extracting points defining the surface of a desired object from the three-dimensional echo data stored in said three-dimensional echo data memory means;
   a shading means for shading data of a surface defined with the points extracted by said surface point extracting means;
   a synthesizing means for synthesizing data of the slices whose positions are set by said slice position setting means and data of the surface shaded by said shading means so as to construct a three-dimensional image; and
   a display means for displaying the three-dimensional image constructed by said synthesizing means,
   wherein said shading means shades data of the surface using the color of an organ as a display color.

16. A diagnostic ultrasonic imaging system, comprising:
   a three-dimensional echo data memory means for transmitting ultrasonic waves to a living body, receiving echoes from the living body, and storing data provided by the echoes emanating from a three-dimensional area;
   a slice position setting means for setting the positions of desired slices using the three-dimensional echo data stored in said three-dimensional echo data memory means;
   a surface point extracting means for extracting points defining the surface of a desired object from the three-dimensional echo data stored in said three-dimensional echo data memory means;
   a shading means for shading data of a surface defined with the points extracted by said surface point extracting means;
   a synthesizing means for synthesizing data of the slices whose positions are set by said slice position setting means and data of the surface shaded by said shading means so as to construct a three-dimensional image; and
   a display means for displaying the three-dimensional image constructed by said synthesizing means,
   wherein said shading means includes a display color designating means for use in designating a display color for the surface, and shades data of the surface in the display color designated with said display color designating means.

17. A diagnostic ultrasonic imaging system, comprising:
   a three-dimensional echo data memory means for transmitting ultrasonic waves to a living body, receiving echoes from the living body, and storing data that is provided by the echoes emanating from a three-dimensional area and represents a plurality of consecutive ultrasonic tomographic images;
   a slice position setting means for setting the positions of desired slices using the three-dimensional echo data stored in said three-dimensional echo data memory means;
   a surface point extracting means for extracting points defining the surface of a desired object from the three-dimensional echo data stored in said three-dimensional echo data memory means;
   a shading means for shading data of a surface defined with the points extracted by said surface point extracting means;
   a synthesizing means for synthesizing data of the slices whose positions are set by said slice position setting means and data of the surface shaded by said shading means so as to construct a three-dimensional image; and
   a display means for displaying the three-dimensional image constructed by said synthesizing means,
   wherein said surface point extracting means includes: a surface point designating means for use in designating points defining the surface of a desired object in a specified tomographic image among a plurality of ultrasonic tomographic images;
   a first gradient calculating means for calculating a gradient in luminance value at points defining a surface which are designated with said surface point designating means;
   a second gradient calculating means for calculating a gradient in luminance value at points within a specified range relative to each point, at which the first gradient is calculated, in tomographic images other than the specified tomographic image; and
   a surface point specifying means for specifying points defining the surface of an object in a tomographic image different from a tomographic image, in which the points defining the surface of an object are designated with said surface point designating means, by comparing the gradients calculated by said second gradient calculating means with the gradients calculated by said first gradient calculating means.

18. A diagnostic ultrasonic imaging system, comprising:
   a three-dimensional echo data memory means for transmitting ultrasonic waves to a living body, receiving echoes from the living body, and storing data that is provided by the echoes emanating from a three-dimensional area and represents a plurality of consecutive ultrasonic tomographic images;
   a slice position setting means for setting the positions of desired slices using the three-dimensional echo data stored in said three-dimensional echo data memory means;
   a surface point extracting means for extracting points defining the surface of a desired object from the three-dimensional echo data stored in said three-dimensional echo data memory means;
   a shading means for shading data of a surface defined with the points extracted by said surface point extracting means;
   a synthesizing means for synthesizing data of the slices whose positions are set by said slice position setting means and data of the surface shaded by said shading means so as to construct a three-dimensional image; and a display means for displaying the three-dimensional image constructed by said synthesizing means, wherein said surface point extracting means includes a surface tracing means for automatically tracing points, which define the surface of a desired object, successively in the plurality of consecutive ultrasonic tomographic images.

19. A diagnostic ultrasonic imaging system according to claim 18, wherein said surface tracing means includes a luminance change point retrieving means for retrieving a luminance value from points on an arc used to search for points defining the surface of a desired object, and thus searching for a point defining the surface as a change point at which the luminance value undergoes a change, and successively traces the points defining the surface of a desired object by setting the change point as a center of the arc.

20. A diagnostic ultrasonic imaging system according to claim 18 or 19, wherein said surface point extracting means includes a tracing start point designating means for use in designating a tracing start point for the purpose of tracing in the ultrasonic tomographic images.

21. A diagnostic ultrasonic imaging system according to any of claims 18, 19, and 20, wherein said surface point extracting means includes a tomographic image constructing means for constructing a plurality of tomographic images depicting differently-oriented slices using image data of the three-dimensional echo data, and said tracing start point designating means is used to designate a tracing start point in a tomographic image depicting a slice whose orientation is different from those depicted by the plurality of consecutive ultrasonic tomographic images constructed by said tomographic image constructing means.

* * * * *